United States Patent [19]
Barrett et al.

[11] Patent Number: 5,643,873
[45] Date of Patent: Jul. 1, 1997

[54] PEPTIDES AND COMPOUNDS THAT BIND SELECTINS INCLUDING ENDOTHELIAL LEUKOCYTE ADHESION MOLECULE 1

[75] Inventors: Ronald W. Barrett, Sunnyvale; Steven E. Cwirla, Palo Alto; William J. Dower, Menlo Park; Kerry J. Koller, San Francisco; Jung Lee, Mountain View; Christine L. Martens, Portola Valley; Beatrice Ruhland-Fritsch, Los Altos, all of Calif.

[73] Assignee: Affymax Technologies N.V., Netherlands, Netherlands Antilles

[21] Appl. No.: 241,054

[22] Filed: May 11, 1994

Related U.S. Application Data

[63] Continuation-in-part of Ser. No. 57,295, May 5, 1993, abandoned, which is a continuation-in-part of Ser. No. 881,395, May 6, 1992, abandoned.

[51] Int. Cl.$^6$ .......................... A61K 38/00; C07K 14/00; C07K 7/08; C07K 7/06
[52] U.S. Cl. .......................... 514/12; 530/324; 530/326; 530/327; 514/13; 514/14; 514/15
[58] Field of Search .......................... 514/14, 15, 12–13; 530/326–327

[56] References Cited

U.S. PATENT DOCUMENTS

| | | |
|---|---|---|
| 4,680,265 | 7/1987 | Birmingham et al. . |
| 5,010,175 | 4/1991 | Rutter et al. . |
| 5,053,392 | 10/1991 | Klein et al. . |
| 5,075,022 | 12/1991 | Hannum et al. . |
| 5,081,034 | 1/1992 | Bevilacqua et al. ............... 435/252.33 |
| 5,143,854 | 9/1992 | Pirrung et al. . |
| 5,166,133 | 11/1992 | Houston et al. . |
| 5,198,424 | 3/1993 | McEver .................................... 514/13 |
| 5,208,253 | 5/1993 | Boschelli . |
| 5,258,289 | 11/1993 | Davis et al. . |
| 5,268,364 | 12/1993 | Kojima et al. . |
| 5,324,591 | 6/1994 | Georger, Jr. et al. . |

FOREIGN PATENT DOCUMENTS

| | | |
|---|---|---|
| 0505749 | 9/1992 | European Pat. Off. . |
| WO90/05539 | 5/1990 | WIPO . |
| WO90/15070 | 12/1990 | WIPO . |
| WO91/05058 | 4/1991 | WIPO . |
| WO91/16900 | 11/1991 | WIPO . |
| WO91/19502 | 12/1991 | WIPO . |
| WO91/19818 | 12/1991 | WIPO . |
| WO92/00995 | 1/1992 | WIPO . |
| WO92/01718 | 2/1992 | WIPO . |
| WO92/02527 | 2/1992 | WIPO . |
| WO92/07572 | 5/1992 | WIPO . |
| WO92/08488 | 5/1992 | WIPO . |
| WO92/09293 | 6/1992 | WIPO . |
| WO92/12729 | 8/1992 | WIPO . |
| WO92/18610 | 10/1992 | WIPO . |
| WO92/19646 | 11/1992 | WIPO . |
| WO92/19735 | 11/1992 | WIPO . |
| WO92/20708 | 11/1992 | WIPO . |
| WO93/05070 | 3/1993 | WIPO . |
| WO93/06865 | 4/1993 | WIPO . |
| WO93/07268 | 4/1993 | WIPO . |
| WO90/13300 | 11/1993 | WIPO . |
| WO93/24526 | 12/1993 | WIPO . |
| WO94/05269 | 3/1994 | WIPO . |
| WO94/05310 | 3/1994 | WIPO . |
| WO94/11498 | 5/1994 | WIPO . |
| WO92/12994 | 8/1994 | WIPO . |
| WO94/17193 | 8/1994 | WIPO . |

OTHER PUBLICATIONS

Hession et al., "Endothelial leukocyte adhesion molecule 1: Direct expression cloning and functional interactions," Cell Biology, *Proceeding of the National Academy of Sciences USA*, 87:1673–1677 (Mar. 1990).

Johnston et al., "Cloning of GMP-140, a Granule Membrane Protein of Platelets and Endothelium: Sequence Similarity to Proteins Involved in Cell Adhesion and Inflammation," *Cell*, 56:1033–1044 (Mar. 1989).

Roemer, et al., PNAS, 88:11295–11299 (1991).

Barrett, Ronald W. et al., "Selective Enrichment and Characterization of High Affinity Ligands from Collections of Random Peptides in Filamentous Phage", *Analytical Biochemistry*, 204, pp. 357–364 (1992).

Bender, Paul E. et al., "Chapter 20. Pharmacological Modulation in Interleukin–1", *Annual Reports in Medicinal Chemistry*, 25, pp. 185–193 (1989).

Bevilacqua et al., "Selectins: A Family of Adhesion Receptors", Letter to the Editor, *Cell*. vol. 67, p. 223, Oct. 18, 1991.

Bochelli, J., "3-Alkoxybenzo[b]thiophene-2-carboxamides as Inhibitors of Neutrophilendothelial Cell Adhesion", *Medical Chem.*, 37(6).

Cho, Charles, Y. et al., "An Unnatural Biopolymer", *Science*, vol. 261, Sep. 3, 1993, pp. 1303–1305.

Collins et al., "Structure and Chromosomal Location of the Gene for Endotheial–Leukocyte Adhesion Molecule 1" (1991) *J. Biol. Chem.*, 266:2466–2473.

Cwirla, Steven E. et al., "Peptides on Phage: A Vast Library of Peptides for Identifying Ligands", *Proc. Natl. Acad. Sci. USA*, vol. 87, Aug. 1990, pp. 6378–6382.

Edington, Stephen M., "How Sweet It Is: Selectin–Mediating Drugs", *Bio/Technology*, vol. 10., Apr. 1992, pp. 383–389.

(List continued on next page.)

*Primary Examiner*—Elizabeth C. Weimar
*Assistant Examiner*—S. G. Marshall
*Attorney, Agent, or Firm*—Townsend and Townsend and Crew LLP

[57] ABSTRACT

Disclosed are peptides and peptide mimetics that bind selectins, including endothelial leukocyte adhesion molecule 1 (ELAM-1). Such peptides and peptide mimetics are useful in methods for blocking adhesion of leukocytes to the selectins for the purpose of inhibiting inflammation as well as in diagnostic methods employing labeled peptides and peptide mimetics that bind selectins for the purpose of determining the site of inflammation in mammals which inflammation is mediated by the presence of one or more selectins.

3 Claims, 5 Drawing Sheets

OTHER PUBLICATIONS

Ezzell, Carol, "Sticky Situations—Picking Apart the Molecules that Glue Cells Together", *Science News*, vol. 141, Jun. 13, 1992, pp. 392–395.

Geng, Jian–Guo et al., "Rapid Neutrophil Adhesion to Activated Endothelium Mediated by GMP–140", *Nature*, vol. 343, Feb. 22, 1990, pp. 757–760.

Goelz, Susan E. et al., "ELFT: A Gene That Directs the Expression of an ELAM–1 Ligand", *Cell.*, vol. 63, Dec. 21, 1990, pp. 1349–1356.

Hession C. et al., "Endothelial Leukocyte Adhesion Molecule 1: Direct Expression Cloning and Functional Interactions", *Proc. Natl. Acad. Sci. USA*, vol. 87 (Cell Biology), Mar. 1990, pp. 1673–1677.

Johnston, Geoffrey I. et al., "Cloning of GMP–140, a Granule Membrane Protein of Platelets and Endothelium: Sequence Similarity to Proteins Involved in Cell Adhesion and Inflammation", *Cell*, pp. 1034–1044 1989.

Oliphant, Arnold R. et al., "Defining the Sequence Specificity of DNA–Binding Proteins by Selecting Binding Sites from Random–Sequence Oligonucleotides: Analysis of Yeast GCN4 Protein", *Molecular and Cellular Biology*, vol. 9, No. 7, Jul. 1989 pp. 2944–2949.

Parekh, Raj. B, "Oligosaccharides as Specific Ligands for the LECAMs", Technical Bulletin No. 11 (TB–11), Oxford GlycoSystems Limited, Abingdon, UK, 1991, pp. 1–6.

Paulson, James C., "Chapter 2 –Selectin/Carbohydrate–Mediated Adhesion of Leukocytes", *Adhesion: Its Role in Inflammatory Disease*, pp. 19–42 1989.

Phillips, Laurie M. et al., "ELAM–1 Mediates Cell Adhesion by Recognition of Carbohydrate Ligand, Sialyl–Le$^x$" *Science*, vol. 250, pp. 1130–1135 1990.

Picker, Louis J. et al., "ELAM–1 is an Adhesion Molecule for Skin–Homing T Cells", *Nature*, vol. 349, Feb. 28, 1991, pp. 796–798.

Polley, Margaret J. et al., "CD62 and Endothelial Cell–Leukocyte Adhesion Molecule 1 (ELAM–1) Recognize the Same Carbohydrate Ligand, Sialyl–Lewis X" *Proc. Natl. Acad. Sci. USA*, vol. 88 (Immunology), Jul. 1991, pp. 6224–6228.

Rice, G. Edgar and Bevilacqua Michael P., "An Inducible Endothelial Cell Surface Glycoprotein Mediates Melanoma Adhesion", *Reports*, Dec. 8, 1989, pp. 1303–1306.

Shimizu, Yoji et al., "Activation–Independent Binding of Human Memory T Cells to Adhesion Molecule ELAM–1", Letters to Nature *Nature*, vol. 349, Feb. 28, 1991, pp. 799–802.

Spertini, Olivier et al., "Regulation of Leukocyte Migration by Activation of the Leukocyte Adhesion Molecule–1 (LAM–1 Selectin)", *Nature*, vol. 349, Feb. 21, 1991, pp. 691–693.

Springer, Timothy A., "Adhesion Receptors of the Immune System", Review Article, *Nature*, vol. 346, Aug. 12, 1990, pp. 425–434.

Tiemeyer, Michael, et al., "Carbohydrate Ligands for Endothelial–Leukocyte Adhesion Molecule 1", *Proc. Natl. Acad. Sci. USA*, vol. 88 (Biochemistry), Feb. 1991, pp. 1138–1142.

Tyrrell David et al., "Structural Requirements for the Carbohydrate Ligand of E–Selectin", *Proc. Natl. Acad. Sci. USA*, vol. 88 (Biochemistry), Nov. 1991, pp. 10372–10376.

PEPTIDES AND COMPOUNDS THAT BIND SELECTINS INCLUDING ENDOTHELIAL LEUKOCYTE ADHESION MOLECULE 1

CROSS-REFERENCE TO RELATED APPLICATIONS

This application is a continuation-in-part of U.S. application Ser. No. 08/057,295 filed May 5, 1993, now abandoned which, in turn, is a continuation-in-part of U.S. application Ser. No. 07/881,395 filed May 6, 1992 now abandoned, the disclosures of both of which are incorporated herein by reference in their entirety.

BACKGROUND OF THE INVENTION

1. Field of the Invention

This invention is directed to peptides and peptide mimetics that bind selectins, including endothelial leukocyte adhesion molecule 1 (ELAM-1). This invention is further directed to methods for blocking adhesion of leukocytes to the selectins for the purpose of inhibiting inflammation, inhibiting tumor metastasis, inhibiting reperfusion injury, and the like. This invention is still further directed to diagnostic methods employing labeled peptides and peptide mimetics that bind selectins for the purpose of determining the site of inflammation in mammals which inflammation is mediated by the presence of one or more selectins.

References

The following references are cited in this application as superscript numbers at the relevant portion of the application:

1 Bevilacqua, et al., *Proc. Natl. Acad. Sci. USA*, 84:9238–9242 (1987)
2 Geng, et al., *Nature*, 343:757–760 (1990)
3 Springer, *Nature*, 346:425–434 (1990)
4 Bevilacqua, et al., *Cell*, 67:233 (1991)
5 Johnston, et al., *Cell*, 56:1033–1044 (1989)
6 Paulson, *Selectin/Carbohydrate-Mediated Adhesion of Leukocytes in Adhesion: Its Role in Inflammatory Disease*, pp. 19–42
7 Springer, et al., *Nature*, 349:196–197 (1991)
8 Lowe, et al., *Cell*, 63:475–485 (1990)
9 Phillips, et al., *Science*, Vol. 250:1130–1132 (1990)
10 Walz, et al., *Science*, 250:1132 et seq. (1990)
11 Larsen, et al., *Cell*, 63:467–474 (1990)
12 Brandley, et al., PCT International Patent Application No. WO 92/02527, published Feb. 20, 1992
13 Furie, et al., PCT International Patent Application No. WO 92/16612, published Oct. 1, 1992
14 Phillips, et al, *Science*, 250:1130–1135 (1990)
15 Parekh, *Oxford GlycoSystems Ltd., Tech. Bull.* 11, (1991)
16 Tiemeyer, et al., *Proc. Natl. Acad. Sci. USA*, 85.:1138–1142 (1991)
17 Tyrrell, et al., *Proc. Natl. Acad. Sci. USA*, 88:10372–10376 (1991)
18 Polley, et al., *Proc. Natl. Acad. Sci. USA*, 88:6224–6228 (1991)
19 Paulson, et al., PCT International Patent Application Publication No. WO 91/19502, published Dec. 26, 1991
20 McEver, PCT International Patent Application Publication No. WO 92/01718, published Feb. 6, 1992
21 Edgington, *Biotechnology*, 10:383–389 (1992)
22 McEver, U.S. Pat. No. 5,198,424 for *Functionally Active Selectin-Derived Peptides*, issued Mar. 30, 1993
23 Heavner, et al., PCT International Patent Application Publication No. WO 93/05070 published Mar. 18, 1993
24 Brandley, et al., U.S. Pat. No. 5,143,712, for *Method for Determining a Cite of Inflammation Using ELAM-1 Ligands*, issued Sep. 1, 1992
25 Bender and Lee, *Ann. Rep. Med. Chem.*, 25:185–193 (1989)
26 Hannum, et al., U.S. Pat. No. 5,075,222, for *Interleukin-1 Inhibitors*, issued Dec. 24, 1991
27 Cwirla, et al., *Proc. Natl. Acad. Sci. USA*, 87:6378–6382 (1990)
28 Pirrung, et al., U.S. Pat. No. 5,143,854, for *Large Scale Photolithographic Solid Phase Synthesis of Polypeptides and Receptor Binding Screening Thereof*, issued Sep. 1, 1992
29 Pirrung, et al., PCT International Patent Application Publication No. 90/15070, published Dec. 13, 1990
30 Fodor, et al., *Science*, 251:767–773 (1991)
32 Dower, et al., *Ann. Rep. Med. Chem.*, 26:271–280 (1991)
33 Caras and Weddell, *Science*, 243:1196–1198, (1989)
34 Lin, et al., *Science*, 249:677–679 (1990)
35 Merrifield, *J. Am. Chem. Soc.*, 85:2149 (1963)
36 Bodonszky, et al., *Chem. Ind.* (London) 38:1597 (1966)
37 Pietta and Marshall, *Chem. Commn.*, 650 (1970)
38 Gisin, *Helv. Chim. Acta*, 56:1487 (1973)
39 Cho, et al., *Science*, 261:1303–1305 (1993)
40 Stewart, *Solid Phase Peptide Syntheses* (Freeman and Co., San Francisco, 1969).
41 Morgan and Gainor, *Ann. Rep. Med. Chem.* 24:243–252 (1989)
42 Hruby et al., *Biochem J.* 268(2):249–262, (1990)
43 *Journal of Organic Chemistry*, 47:1324–1326 (Procedure C) (1982)
44 *Tetrahedron*, 39:475 (1983)

The disclosure of all publications, patents and patent applications cited in this application are herein incorporated by reference in their entirety to the same extent as if each individual publication or patent application was specifically and individually indicated to be incorporated by reference in its entirety.

State of the Art

The accumulation of blood leukocytes at sites of mammalian inflammation depends upon the localization of these leukocytes by adhesion to the vascular endothelium and subsequent extravasation of the leukocytes. Certain cytokines, such as interleukin 1 (IL-1) and tumor necrosis factor alpha and beta (TNF-α and TNF-β respectively), as well as bacterial endotoxin, have been shown to act on cultured human endothelial cells to increase leukocyte adhesion. Bevilacqua, et al.[1] report the identification of an inducible endothelial cell surface protein with a molecular weight of about 115 kD, designated endothelial leukocyte adhesion molecule 1 (ELAM-1, also known as LECAM-2, CD62E, and E-selectin) which protein is involved in the process of leukocyte adhesion to the vascular endothelium prior to extravasation of leucocytes through the endothelium to the site of inflammation.

Further studies have shown that the E-selectin is a member of a family of receptors referred to as "selectins" which family includes other known receptors such as PADGEM (also known as the P-selectin, GMP-140, LECAM-3 and CD62P) and LAM-1 (also known as the L-selectin, LECAM-1, MEL-14 and CD62L)[2,3,4,5]. Each of these other selectins is also involved in the process of leukocyte adhesion to the vascular endothelium prior to extravasation of leukocytes through the endothelium to the site of inflammation.

Homologous to each of these known selectin proteins is an N-terminal lectin domain, an epidermal growth factor (EGF) like domain, a number of repeating units related to those in complement binding proteins, a transmembrane domain, and a short cytoplasmic tail[6]. Evidence suggests that the in vivo ligands for these selectin proteins are glycoconjugates which purportedly bind to the selectin through, at least in part, the carbohydrate portion of the glycoconjugate. The carbohydrate structures of such ligands include structures containing terminally linked αNeu5Ac (2→3)βGal(1→4)-[α-L-Fuc (1→3)]-βGlcNAc- (sialyl Lewis$^x$ or SLe$^x$) which structures are part of the cell surface glycoprotein and glycolipid groups of neutrophils for the E- and the P-selectin and of endothelial cells for the L-selectin during adhesion.[7–18]

In view of their binding to selectins, the administration of SLe$^x$ and related carbohydrates has been proposed as a means for controlling inflammatory conditions and other conditions mediated by selectin proteins by interfering with leukocyte adhesion to these proteins[12–13,19–20]. Such inflammatory conditions mediated by selectin proteins include, by way of example, (1) dermal inflammation, including Il-1-induced skin inflammation; atopic dermatitis, psoriasis, and allergic contact dermatitis; delayed-type hypersensitivity reaction induced by DNCB on human skin; and endotoxin-induced acute cutaneous inflammation in baboons; (2) intestinal inflammation, including inflamed colonic mucosa of patients with ulcerative or Crohn's colitis; inflammatory bowel disease; and intestinal graft-versus-host disease; (3) other sites of inflammation, including synovial tissues from patients with rheumatoid arthritis and osteo arthritis; rat endotoxin-induced uveitis, and inflamed endothelium of asthma model (primate antigen inhalation), acute respiratory distress syndome (ARDS); and (4) septic shock.[25,26]

Central to such disclosures is the administration to the patient of a carbohydrate structure which binds to the selectin thereby preventing binding of the selectin protein with the carbohydrate binding structures found on the cell surface of the neutrophils or on the endothelium.

It has also been disclosed to use such carbohydrates for diagnostic purposes in identifying in vivo the sites of the E-selectin expression[23,24]. Such information is important in the treatment of E-selectin mediated conditions such as tissue damage associated with myocardial infarction, inflammation, etc. Additionally, it has also been suggested to couple anti-inflammatory drugs to the carbohydrate ligands of E-selectin to provide for site specific drug delivery to the point of inflammation[19,24].

The use of carbohydrate structures as part of either the treatment regimen for E-selectin mediated conditions (e.g., inflammatory conditions) or diagnosis of sites of E-selectin mediated conditions is complicated, however, by the fact that these compounds are difficult to synthesize and, using conventional synthetic procedures, costs for preparation of such carbohydrates are prohibitive[21].

Contrarily, it has also been suggested to use polyclonal/ monoclonal antibodies to selectins, e.g., E-selectin, as well as peptides derived from the lectin-like domain of the P-selectin for the purpose of interfering with leukocyte/ selectin binding[22,23] in a therapeutic regimen.

In the case of peptides derived from the lectin-like domain of the P-selectin, it is disclosed that these materials have the binding properties of selectins and can bind neutrophils. When administered, these peptides compete with the selectins for binding to neutrophils and such competition can be therapeutically used to inhibit conditions mediated by selectin/neutrophil interactions such as, for example, inflammatory conditions.

In the case of polyclonal/monoclonal antibodies, it has been disclosed that these materials bind directly to the selectin thereby inhibiting the ability of neutrophils to bind to selectins. Inhibition of the neutrophil/selectin binding can be used therapeutically for conditions mediated by selectins.

However, therapeutic use of such polyclonal/monoclonal antibodies is not favored because such antibodies are typically immunogenic and administration is usually limited to a single occurrence[22]. In such cases, additional administrations of such antibodies can produce an adverse reaction in the patient.

Likewise, the use of peptides having binding properties of selectins is not favored because such peptides typically do not bind selectins and, accordingly, are not suitable for use in the in vivo diagnosis of sites of E-selectin expression which correlates to disease conditions mediated by E-selectin including inflammatory conditions. Nor can these peptides be used for the site specific delivery of anti-inflammatory or other drugs suitable for treatment of conditions mediated by E-selectin.

SUMMARY OF THE INVENTION

This invention is directed, in part, to the novel and unexpected discovery that defined low molecular weight peptides and peptide mimetics have strong binding properties to E-selectin and, in some cases, to the other selectins, i.e., the P-selectin and L-selectin. Accordingly, such peptides and peptide mimetics are useful for therapeutic purposes in treating conditions mediated by E-selectin (e.g., inflammatory conditions) as well as for diagnostic purposes in identifying in vivo the vascular site of E-selectin protein and, hence, the site of conditions mediated by E-selectin expression. Such peptides and peptide mimetics can also be coupled to anti-inflammatory drugs or other drugs suitable for treatment of the disease conditions mediated by E-selectin expression so as to provide for in vivo site specific drug delivery to the point of E-selectin expression.

Peptides and peptide mimetics suitable for diagnostic purposes are Characterized by having a molecular weight of less than about 2000 daltons and a binding affinity to E-selectin as expressed by an $IC_{50}$-HL60 of about no more than about 100 μM as determined by the HL60 binding affinity assay set forth in Example 1 and preferably no more than 50 μM.

In one preferred embodiment, the molecular weight of the peptide or peptide mimetic is from about 250 to about 1800 daltons.

In another preferred embodiment, the $IC_{50}$ binding affinity of the peptide or peptide mimetic is determined by binding competition between a candidate peptide and a standard as per the in vitro procedure provided in Example 2 hereinbelow. This example measures the concentration of peptide or peptide mimetic required to inhibit 50% of the binding of a radiolabeled standard to E-selectin and the resulting $IC_{50}$ value is referred to as the "$IC_{50}$-standard". In either case, a lower $IC_{50}$-HL60 or a lower $IC_{50}$-standard for the peptide or peptide mimetic correlates to a stronger binding affinity to E-selectin.

Preferably, the peptide or peptide mimetic has an $IC_{50}$-standard of about 2.5 mM or less. For therapeutic purposes, these peptides and peptide mimetics preferably have a molecular weight of less than about 2000 daltons and a binding affinity to E-selectin as expressed by an $IC_{50}$-standard of about 2.0 mM or less. In a more preferred embodiment, the peptide or peptide mimetic has an $IC_{50}$-standard of about 2.5 μM or less and even more preferably has an $IC_{50}$-standard of about 10 nM or less.

When used for diagnostic purposes, the peptides and peptide mimetics preferably are labeled with a detectable label and, accordingly, the peptides and peptide mimetics without such a label serve as intermediates in the preparation of labeled peptides and peptide mimetics.

Peptides meeting the defined criteria for molecular weight and binding affinity for E-selectin comprise 3 or more amino acids wherein the amino acids are naturally occurring or synthetic (non-naturally occurring) amino acids. Peptide mimetics include peptides having one or more of the following modifications:

peptides wherein one or more of the peptidyl [C(O)NH—] linkages (bonds) have been replaced by a non-peptidyl linkage such as a —CH$_2$-carbamate linkage [—CH$_2$—OC(O)NR—], a phosphonate linkage, a —CH$_2$-sulfonamide [—CH$_2$—S(O)$_2$NR—] linkage, a urea [—NHC(O)NH—] linkage, a —CH$_2$-secondary amine linkage, or with an alkylated peptidyl linkage [—C(O)NR$^6$— where R$^6$ is lower alkyl], peptides wherein the N-terminus is derivatized to a —NRR$^1$ group, to a —NRC(O)R group, to a —NRC(O)OR group, to a —NRS(O)$_2$R group, to a —NHC(O)NHR group where R and R$^1$ are hydrogen or lower alkyl with the proviso that R and R$^1$ are not both hydrogen, to a succinimide group, i.e.,

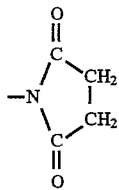

to a benzyloxycarbonyl-NH— (CBZ—NH—) group, i.e.,

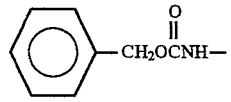

to a benzyloxycarbonyl-NH— group having from 1 to 3 substituents on the phenyl ring selected from the group consisting of lower alkyl, lower alkoxy, chloro, and bromo, peptides wherein the C terminus is derivatized to —C(O)R$^2$ where R$^2$ is selected from the group consisting of lower alkoxy, and —NR$^3$R$^4$ where R$^3$ and R$^4$ are independently selected from the group consisting of hydrogen and lower alkyl.

Accordingly, in a first compositional aspect, this invention is directed to peptides and peptide mimetics comprising:

a molecular weight of less than about 2000 daltons, and a binding affinity to endothelial leukocyte adhesion molecule 1 as expressed by an IC$_{50}$-HL60 of no more than about 100 μM wherein from zero to all of the —C(O)NH— linkages of the peptide have been replaced by a linkage selected from the group consisting of a —CH$_2$OC(O)NR— linkage, a phosphonate linkage, a —CH$_2$S(O)$_2$NR— linkage, a —CH$_2$NR— linkage, a —C(O)NR$^6$— linkage, and a —NHC(O)NH— linkage where R is hydrogen or lower alkyl, and R$^6$ is lower alkyl, further wherein the N-terminus of said peptide or peptide mimetic is selected from the group consisting of a —NRR$^1$ group, a —NRC(O)R group, a —NRC(O)OR group, a —NRS(O)$_2$R group, a —NHC(O)NHR group, a succinimide group, a benzyloxycarbonyl-NH— group, and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide and physiologically acceptable salts thereof.

In a second compositional aspect, this invention is directed to a labeled peptide or peptide mimetic comprising:

a molecular weight of less than about 2000 daltons, a binding affinity to endothelial leukocyte adhesion molecule 1 as expressed by an IC$_{50}$-HL60 of about 100 μM or less, and having covalently attached thereto a label capable of detection wherein from zero to all of the —C(O)NH— linkages of the peptide have been replaced by a linkage selected from the group consisting of a —CH$_2$OC(O)NR— linkage, a phosphonate linkage, a —CH$_2$S(O)$_2$NR— linkage, a —CH$_2$NR— linkage, a —C(O)NR$^6$— linkage, and a —NHC(O)NH— linkage where R is hydrogen or lower alkyl, and R$^6$ is lower alkyl, further wherein the N-terminus of said peptide or peptide mimetic is selected from the group consisting of a —NRR$^1$ group, a —NRC(O)R group, a —NRC(O)OR group, a —NRS(O)$_2$R group, a —NHC(O)NHR group, a succinimide group, a benzyloxycarbonyl-NH— group, and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide and physiologically acceptable salts thereof.

Preferably, the peptides and peptide mimetics described above have an IC$_{50}$-standard, as measured in Example 2 hereinbelow, of about 2.5 mM or less. Peptides having such an IC$_{50}$-standard define a subclass of peptides meeting the IC$_{50}$-HL60 requirements of 100 μM or less which have stronger binding affinity to endothelial leukocyte adhesion molecule 1. In a more preferred embodiment, the peptide or peptide mimetic has an IC$_{50}$-standard of about 2.0 μM or less and even more preferably has an IC$_{50}$-standard of about 10 nM or less.

Preferred peptides for use in this invention include peptides having a core structure comprising:

WXXLWXXM (SEQ ID NO 1)
where each amino acid is indicated by the one letter amino acid symbols recommended by the IUPAC-IUB Biochemical Nomenclature Commission where W is tryptophan, L is leucine, M is methionine, and X is any amino acid.

Other preferred peptides include peptides 9 to 12 amino acid residues in length and comprising the sequence $X_1X_2X_3WX_4X_5LWX_6X_7X_8X_9$ (SEQ ID NO 2), wherein each residue can be independently selected as follows: $X_1$, is H, E, or D; $X_2$ is I, M, or Nle; $X_3$ is T or S; $X_4$ is D, A, E, or L; $X_5$ is Q or E; $X_6$ is N or D; $X_7$ is L, M, V, or I; $X_8$ is M or Nle; and $X_9$ is N, S, K, or Q. $X_8$ can also include methionine derivatives such as O-methyl methionine ($MOCH_3$) and met-sulfone ($MSO_2CH_3$) as described below.

Still other preferred peptides of the invention include peptides that comprise the following sequences:

DITWDQLWDLMK (SEQ ID NO 3)
DGDITWDQLWDLMK (SEQ ID NO 4)
DYTWFELWDMMQ (SEQ ID NO 5)
DITWDELWKIMN (SEQ ID NO 6)
QITWAQLWNMMK (SEQ ID NO 7)
DYSWHDLWEMMS (SEQ ID NO 8)
DITWDQLWDLNleK (SEQ ID NO 9)
HITWDQLWRIMT (SEQ ID NO 10)
d-DITWDQLWDLMK
Dd-ITWDQLWDLMK
ITWDQLWDLMK (SEQ ID NO 160)
HITWDQLWNVMN (SEQ ID NO 23)

wherein d- indicates a D-amino acid.

Other peptides suitable for use in this invention include peptides which comprise the following sequences:

YDDVCCELLF (SEQ ID NO 11)
DLPQWYTEWC (SEQ ID NO 12)
ENSHWCTCPC (SEQ ID NO 13)
DIEQDWVTWM (SEQ ID NO 14)
NEWCVVPCRL (SEQ ID NO 15)
DIWQDWVRWM (SEQ ID NO 16)
DLWQDWVTWM (SEQ ID NO 17)
DLWQDWVHWM (SEQ ID NO 18)
DIWQDWVTWM (SEQ ID NO 19)
DIWQDWVKWM (SEQ ID NO 20)
DIWQDWVRWM-NH$_2$ (SEQ ID NO 164)
DIWEDWVRWM (SEQ ID NO 21)
DIWQDWITWM (SEQ ID NO 22)

This invention also provides for pharmaceutical compositions comprising peptides and peptide mimetics and a pharmaceutically acceptable carrier wherein said peptides and peptide mimetics comprise:

a molecular weight of less than about 2000 daltons, and a binding affinity to endothelial leukocyte adhesion molecule 1 as expressed by an $IC_{50}$-HL60 of no more than 100 μM wherein from zero to all of the —C(O)NH— linkages of the peptide have been replaced by a linkage selected from the group consisting of a —CH$_2$OC(O)NR— linkage, a phosphonate linkage, a —CH$_2$S(O)$_2$NR— linkage, a —CH$_2$NR— linkage, a —C(O)NR$^6$— linkage, and a —NHC(O)NH— linkage where R is hydrogen or lower alkyl, and R$^6$ is lower alkyl, further wherein the N-terminus of said peptide or peptide mimetic is selected from the group consisting of a —NRR$^1$ group, a —NRC(O)R group, a —NRC(O)OR group, a —NRS(O)$_2$R group, a —NHC(O)NHR group, a succinimide group, a benzyloxycarbonyl-NH— group, and a benzyloxycarbonyl-NH— group having from 1 to 3 substituents on the phenyl ring selected from the group consisting of lower alkyl, lower alkoxy, chloro, and bromo, where R and R$^1$ are independently selected from the group consisting of hydrogen and lower alkyl, and still further wherein the C-terminus of said peptide or peptide mimetic has the formula —C(O)R$^2$ where R$^2$ is selected from the group consisting of hydroxy, lower alkoxy, and —NR$^3$R$^4$ where R$^3$ and R$^4$ are independently selected from the group consisting of hydrogen and lower alkyl and where the nitrogen atom of the —NR$^3$R$^4$ group can optionally be the amine group of the N-terminus of the peptide so as to form a cyclic peptide and physiologically acceptable salts thereof.

This invention still further comprises methods for inhibiting the binding of ligands to selectin receptors, including the binding of SLe$^x$ present on leukocytes to E-selectin, and methods for treating disease and disease symptoms which are mediated by the presence of selectins which methods comprise the administration to a patient of a sufficient amount of a pharmaceutical composition as described above so as to provide for from about 0.001 to about 20 milligrams of such peptides or peptide mimetics per kilogram of body weight daily in the patient. Preferably, administration to the patient provides from about 0.001 to about 15 milligrams and more preferably from about 0.001 to about 10 milligrams of such peptide per kilogram of bodyweight daily.

BRIEF DESCRIPTION OF THE FIGURES

In FIG. 3A, a binding assay is conducted in which the specificity of a peptide for immobilized E-selectin receptor is related to the amount of signal generated by alkaline phosphatase (AP) conjugated to anti-LacI antibodies in turn bound to LacI-peptide fusion proteins. In FIG. 3B, the $IC_{50}$-standard of free peptides in solution is measured in a competition assay.

DETAILED DESCRIPTION OF THE INVENTION

Figure 1:
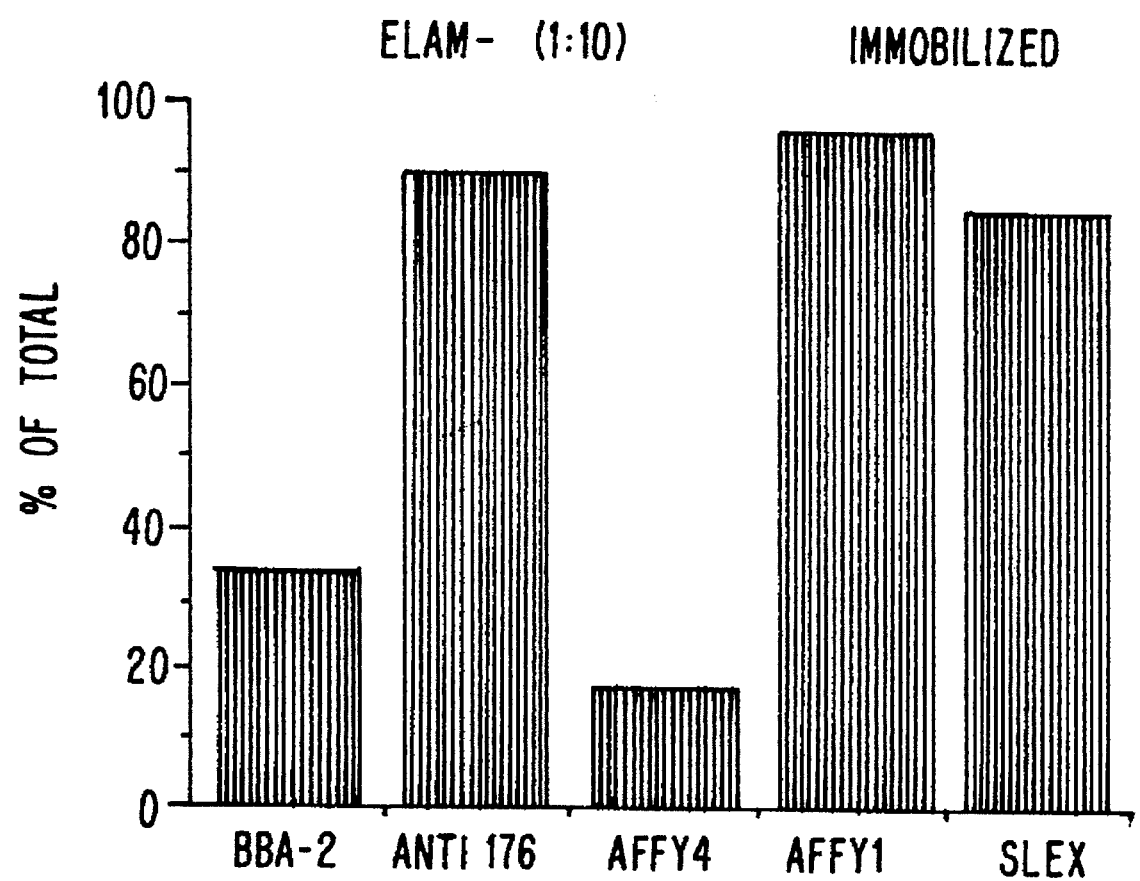
FIG. 1 illustrates the results of a cell adhesion assay in the presence of various peptides; the assay is described in Example 1.

This invention is directed to the discovery that certain defined low molecular weight peptides and peptide mimetics have strong binding properties to E-selectin and, accordingly, are useful in the treatment of disease conditions mediated by E-selectin as well as in diagnostic assays wherein the presence of E-selectin is diagnostic for the site of inflammation and/or other disease conditions mediated by E-selectin expression.

However, prior to discussing this invention in further detail, the following terms will first be defined.

Definitions

As used herein, the following terms have the following meanings:

The term "physiologically acceptable salts" refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate salts, and the like. The particular salt employed is not critical.

The term "lower alkyl" refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 2-methylpentyl, and the like. Preferably, the lower alkyl group is methyl or ethyl.

The term "lower alkoxy" refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 2-methylpentoxy, and the like. Usually, the lower alkoxy group is methoxy or ethoxy.

Naturally occurring amino acid residues in peptides are abbreviated as recommended by the IUPAC —IUB Biochemical Nomenclature Commission as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is LyS or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occuring amino acids refer to amino acids which do not naturally occur in vivo but which, nevertheless, can be incorporated into the peptide structures described herein.

Preferred synthetic amino acids are the D-α-amino acids of naturally occurring L-α-amino acid as well as non-naturally occurring D- and L-α-amino acids represented by the formula $H_2NCHR^5COOH$ where $R^5$ is 1) a lower alkyl group, 2) a cycloalkyl group of from 3 to 7 carbon atoms, 3) a heterocycle of from 3 to 7 carbon atoms and 1 to 2 heteroatoms selected from the group consisting of oxygen, sulfur, and nitrogen, 4) an aromatic residue of from 6 to 10 carbon atoms optionally having from 1 to 3 substituents on the aromatic nucleus selected from the group consisting of hydroxyl, lower alkoxy, amino, and carboxyl, 5) -alkylene-Y where alkylene is an alkylene group of from 1 to 7 carbon atoms and Y is selected from the group consisting of (a) hydroxy, (b) amino, (c) cycloalkyl and cycloalkenyl of from 3 to 7 carbon atoms, (d) aryl of from 6 to 10 carbon atoms optionally having from 1 to 3 substituents on the aromatic nucleus selected from the group consisting of hydroxyl, lower alkoxy, amino and carboxyl, (e) heterocyclic of from 3 to 7 carbon atoms and 1 to 2 heteroatoms selected from the group consisting of oxygen, sulfur, and nitrogen, (f) —C(O)$R^2$ where $R^2$ is selected from the group consisting of hydrogen, hydroxy, lower alkyl, lower alkoxy, and —$NR^3R^4$ where $R^3$ and $R^4$ are independently selected from the group consisting of hydrogen and lower alkyl, (g) —$S(O)_nR^6$ where n is an integer from 1 to 2 and $R^6$ is lower alkyl and with the proviso that $R^5$ does not define a side chain of a naturally occurring amino acid.

Other preferred synthetic amino acids include amino acids wherein the amino group is separated from the carboxyl group by more than one carbon atom such as β-alanine, γ-aminobutyric acid, and the like.

Particularly preferred synthetic amino acids include, by way of example, the D-amino acids of naturally occurring L-amino acids, L-1-napthyl-alanine, L-2-naphthylalanine, L-cyclohexylalanine, L-2-amino isobutyric acid, the sulfoxide and sulfone derivatives of methionine

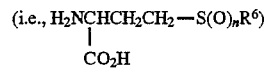

where n and $R_6$ are as defined above as well as the lower alkoxy derivative of methionine

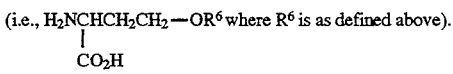

The term "detectable label" refers to materials, which when covalently attached to the peptides and peptide mimetics of this invention, permit detection of the peptide and peptide mimetics in vivo in the patient to whom the peptide or peptide mimetic has been administered. Suitable detectable labels are well known in the art and include, by way of example, radioisotopes, fluorescent labels (e.g., fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of the detectable label to the peptide or peptide mimetic is accomplished by conventional methods well known in the art. For example, when the $^{125}I$ radioisotope is employed as the detectable label, covalent attachment of $^{125}I$ to the peptide or the peptide mimetic can be achieved by incorporating the amino acid tyrosine into the peptide or peptide mimetic and then iodating the peptide. If tyrosine is not present in the peptide or peptide mimetic, incorporation of tyrosine to the N or C terminus of the peptide or peptide mimetic can be achieved by well known chemistry. Likewise, $^{32}P$ can be incorporated onto the peptide or peptide mimetic as a phosphate moiety through, for example, a hydroxyl group on the peptide or peptide mimetic using conventional chemistry.

Methodology

This invention provides peptides and peptide mimetics having strong binding properties to E-selectin characterized as having a binding affinity to E-selectin as expressed by an $IC_{50}$-HL60 of about 100 μM or less and more preferably by an $IC_{50}$-standard of about 2.5 mM. The methods described hereinbelow illustrate in vitro procedures for identifying peptides having such binding properties and procedures for altering such peptides to provide for peptide mimetics having such binding properties to E-selectin.

A. Identification of Peptides Which Bind E-Selectin

Peptides having a binding affinity to E-selectin can be readily identified by random peptide diversity generating systems coupled with an affinity enrichment process.

Specifically, random peptide diversity generating systems include both the "peptides on plasmids" described in U.S. patent application Ser. No. 07/963,321, filed on Oct. 15, 1992, which is a continuation-in-part of U.S. patent application Ser. No. 07/778,233, filed on Oct. 16, 1991, (now U.S. Pat. No. 5,270,170) and the "peptides on phage" system described in U.S. patent application Ser. No. 07/718,577, filed Jun. 20, 1991; in Cwirla et al.[27], in the "encoded synthetic library" (ESL) system described in U.S. patent application Ser. No. 07/946,239, filed Sep. 18, 1992; and the "very large scale immobilized polymer synthesis" system described in U.S. patent application Ser. No. 5,143,85428; International Patent Application Serial No. 90/1507029; U.S. patent application Ser. No. 07/624,120, filed Dec. 6, 1990, Fodor et al.[30], Dower et al.[31], and U.S. patent application Ser. No. 07/805,727,.filed Dec. 6, 1991, the disclosures of each of which are incorporated herein by reference in their entirety.

Using the procedures described above, random peptides were generally designed to have a defined number of amino acid residues in length (e.g., 12). To generate the collection of oligonucleotides encoding the random peptides, the codon motif $(NNK)_x$, where N is nucleotide A, C, G, or T (equimolar; depending on the methodology, other nucleotides can be employed), K is G or T (equimolar), and x is an integer corresponding to the number of amino acids in the peptide (e.g., 12), was used to specify any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

In the systems employed, the random peptides were presented either on the surface of a phage particle, as part of a fusion protein comprising either the pIII or the pVIII coat protein of a phage fd derivative (peptides on phage), or as a fusion protein with the LacI peptide fusion protein bound to a plasmid (peptides on plasmids).

The phage or plasmids, including the DNA encoding the peptides, were identified and isolated by an affinity enrichment process using immobilized E-selectin. The affinity enrichment process, sometimes called "panning," involves multiple rounds of incubating the phage or plasmids with immobilized E-selectin, collecting the phage or plasmids that bind to E-selectin (along with the accompanying DNA), and producing more of the phage or plasmids (along with accompanying LacI-peptide fusion protein) collected.

After several rounds of affinity enrichment, the phage or plasmids and accompanying peptides were examined by ELISA to determine if the peptides bind specifically to E-selectin. This assay was carried out similarly to the procedures used in the affinity enrichment process, except that after removing unbound phage (or plasmids), the wells were typically treated with rabbit anti-phage antibody, then with alkaline phosphatase (AP)-conjugated goat anti-rabbit antibody, or with anti-LacI-AP, as shown in FIG. 3, part A, and then the amount of alkaline phosphatase in each well was determined by standard methods.

By comparing test wells with control wells (no receptor), one can determine whether a peptide binds to E-selectin specifically. Peptides found to bind specifically to E-selectin were then synthesized as the free peptide (no phage) and tested in an HL60 cell adhesion competition assay. The competition assay was carried out similarly to the ELISA, except that labeled HL60 cells were added in addition to the peptide [the control wells were typically of at least two types: (1) no immobilized E-selectin; and (2) no peptide; see Example 1]. In this regard, HL60 cells are known to contain surface glycoconjugates which bind to E-selectin.

Peptides that block the binding of labeled HL60 cells to E-selectin are then evaluated to determine their $IC_{50}$-HL60 in the manner also specified in Example 1. Accordingly, the above methods provide in vitro procedures for readily ascertaining peptides which bind to E-selectin as well as determining the $IC_{50}$-HL60 of such binding peptides in the assay described in Example 1 and peptides which have an $IC_{50}$-HL60 of 100 µM or less are deemed to bind to E-selectin.

Using this assay, the peptide HITWDQLWNVMN (SEQ ID NO 23) was determined to have an $IC_{50}$-HL60 of 50 µM and the peptide DITWDQLWDLMK (SEQ ID NO 3) was determined to have an $IC_{50}$-HL60 of 10 µM.

This latter peptide has strong binding affinity to E-selectin and, accordingly, was used as a standard in a competitive binding assay with candidate peptides and peptide mimetics in order to determine relative binding affinities for E-selectin. This competitive binding assay is conducted in the manner described in Example 2 hereinbelow and that amount of peptide or peptide mimetic which inhibits by 50% the binding of the peptide DITWDQLWDLMK (SEQ ID NO 3) to E-selectin is defined as the $IC_{50}$-standard for that compound. Peptides and peptide mimetics having an $IC_{50}$-standard of about 2.5 mM or less define a preferred set of peptides and peptide mimetics having a greater binding affinity to E-selectin as measured by an $IC_{50}$-HL60 of 100 µM.

The immobilized E-selectin used in the affinity enrichment and ELISA procedures was produced in recombinant host cells in a truncated form comprising the complete extracellular domain (amino acids 1 through 554). The DNA encoding E-selectin is commercially available (R&D Systems, 614 McKinley Place NE, Minneapolis, Minn., 55413 USA as product code BBG57). This truncated E-selectin molecule can be produced in a variety of different forms and host cells. One useful form of E-selectin is constructed by expressing the protein as a soluble protein in baculovirus transformed host cells using standard methods; another useful form is constructed with a signal peptide for protein secretion and for glycophospholipid membrane anchor attachment. This form of anchor attachment is called "PIG-tailing;" see Caras and Weddell[33], and Lin, et al.[34]

Using the PIG-tailing system, one can cleave the E-selectin receptor from the surface of the cells expressing E-selectin (e.g., transformed CHO cells selected for high level expression of E-selectin with a cell sorter) with phospholipase C. The cleaved E-selectin still comprises a carboxy terminal sequence of amino acids, called the "HPAP tail," from the signal for membrane attachment and can be immobilized without further purification.

The recombinant receptor protein can be immobilized by coating the wells of microtiter plates with an anti-HPAP tail antibody, blocking non-specific binding with bovine serum albumin (BSA) in PBS, and then binding cleaved recombinant, truncated E-selectin to the antibody. Using this procedure, one should perform the immobilization reaction in varying concentrations of E-selectin to determine the optimum amount for a given preparation, because different preparations of recombinant protein often contain different amounts of the desired protein. In addition, one should ensure that the immobilizing antibody is completely blocked (with E-selectin or some other blocking compound) during the affinity enrichment process. Otherwise, unblocked antibody can bind undesired phage during the affinity enrichment procedure. One can use peptides that bind to the immobilizing antibody to block unbound sites that remain after ELAM-1 immobilization to avoid this problem or one can simply immobilize the receptor directly to the wells of microtiter plates, without the aid of an immobilizing antibody. See U.S. patent application Ser. No. 07/947,339, filed Sep. 18, 1992, incorporated herein by reference.

When using random peptide generation systems that allow for multivalent ligand-receptor interaction, one must recognize that the density of the immobilized receptor is an important factor in determining the affinity of the ligands that can bind to the immobilized receptor. At higher receptor densities (e.g., each anti-receptor antibody-coated well treated with 0.25 to 0.5 μg of receptor), multivalent binding is more likely to occur than at lower receptor densities (e.g., each anti-receptor antibody-coated well treated with 0.5 to 1 ng of the receptor). If multivalent binding is occurring, then one will be more likely to isolate ligands with relatively lower affinity, unless one uses high densities of immobilized receptor to identify lead compounds and uses lower receptor densities to isolate derivative compounds with higher affinity for the receptor than the lead compounds.

Preferred screening methods to facilitate identification of peptides which bind E-selectin involve first identifying lead peptides which bind E-selectin and then making other peptides which resemble the lead peptide. Specifically, using the pIII-based peptides on phage system, a 12-mer library was screened to discover a phage that presents a peptide that binds to E-selectin. The phage DNAs were sequenced to determine the sequences of the peptides displayed on the surface of the phages. Sequencing revealed that all phage displayed the same peptide. The peptide had the amino acid sequence: HITWDQLWNVMN (SEQ ID NO 23). This peptide can block the adhesion of HL60 cells to immobilized E-selectin and, as noted elsewhere, had an $IC_{50}$-HL60 of 100 μM (see Example 1).

This peptide sequence serves as the basis for the construction of another peptide library designed to contain a high frequency of derivatives of the peptide. Such a library can be synthesized so as to favor the production of peptides that differ from the binding peptide in only a few residues. This approach involves the synthesis (e.g., chemical synthesis) of an oligonucleotide with the binding peptide coding sequence, except that rather than using pure preparations of each of the four nucleoside triphosphates in the synthesis, one uses mixtures of the four nucleoside triphosphates (i.e., 55% of the "correct" nucleotide, and 15% each of the other three nucleotides is one preferred mixture for this purpose and 70% of the "correct" nucleotide, and 10% each of the other three nucleotides is another preferred mixture for this purpose) so as to generate derivatives of the binding peptide coding sequence.

A variety of mutagenesis strategies were used to derivatize the lead peptide by making "mutagenesis on a theme" libraries, which included mutagenesis of the original coding sequence at 70:10:10:10 and 55:15:15:15 frequencies; fixed-sliding libraries, such as HITWDQXXXXXX (SEQ ID NO 24), XXTWDQLWXXXX (SEQ ID NO 25), XXXXDQLWNVXX (SEQ ID NO 26), and XXXXXXLWNVMN (SEQ ID NO 27); an extended/mutagenized library, XXXX-HITWDQLWNVMNXXXX (70:10:10:10) (SEQ ID NO 28), which was screened using standard and modified [200 μM of E-selectin binding peptide QITWAQLWNMMK (SEQ ID NO 7) for 2 hours, followed by glycine-HCl] elution conditions; and libraries with fixed amino acids, such as XXXWXXLWXXMX (SEQ ID NO 29) and XXXX-WXXLWXXMXXXXXX (SEQ ID NO 30) produced in a peptides-on-plasmids system and tested under standard and low receptor density conditions. Screening such libraries yielded the E-selectin-binding peptides shown in Table 1 below.

TABLE 1

| | |
|---|---|
| HITWDQLWNVMN (SEQ ID NO 23) | AITWDQLWLLMS (SEQ ID NO 31) |
| ELTWDQLWVLMS (SEQ ID NO 32) | DVTWDQLWELMT (SEQ ID NO 33) |
| EVTWDQLWVMMQ (SEQ ID NO 34) | NLTWDQLWVLMS (SEQ ID NO 35) |
| EMSWLELWNVMN (SEQ ID NO 36) | TITWDQLWQMMS (SEQ ID NO 37) |
| ELSWDQLWNVMN (SEQ ID NO 38) | EMTWQELWNVMN (SEQ ID NO 39) |
| EMTWTELWNVMN (SEQ ID NO 40) | DMTWSQLWNVMN (SEQ ID NO 41) |
| EMTWLGLWNVMN (SEQ ID NO 42) | QITWMELWNLMN (SEQ ID NO 43) |
| EITWDQLWEVMN (SEQ ID NO 44) | EITWDQLWDVMN (SEQ ID NO 45) |
| DISWDQLWNVMN (SEQ ID NO 46) | QITWDQLWDLMK (SEQ ID NO 47) |
| EMTWDQLWNVMN (SEQ ID NO 48) | DITWDQLWNMMD (SEQ ID NO 49) |
| DITWNMLWNMMQ (SEQ ID NO 50) | DISWDDLWTMMN (SEQ ID NO 51) |
| DITWHQLWNLMN (SEQ ID NO 52) | EISWEQLWTMMN (SEQ ID NO 53) |
| DITWEQLWNMMN (SEQ ID NO 54) | EITWDQLWTLMT (SEQ ID NO 55) |
| DITWHQLWNLMN (SEQ ID NO 56) | DMTWDQLWTVMN (SEQ ID NO 57) |
| DITWEQLWNLMN (SEQ ID NO 58) | QITWYQLWNMMN (SEQ ID NO 59) |
| HISWHELWNLMQ (SEQ ID NO 60) | YITWEQLWTMMN (SEQ ID NO 61) |
| HITWDQLWDLMQ (SEQ ID NO 62) | QITWDQLWDLMY (SEQ ID NO 63) |
| QITWDQLWNMMI (SEQ IO NO 64) | QITWAQLWNMMK (SEQ ID NO 7) |
| YITWEQLWNMMN (SEQ ID NO 65) | HITWDQLWDIMS (SEQ ID NO 66) |
| HITWDQLWEIMS (SEQ ID NO 67) | HITWDQLWALMT (SEQ ID NO 68) |
| HITWDQLWSLMS (SEQ ID NO 69) | HITWDQLWLMMS (SEQ ID NO 70) |
| HITWDQLWDLMQ (SEQ ID NO 71) | HITWDQLWWIMA (SEQ ID NO 72) |
| HITWDQLWLLMA (SEQ ID NO 73) | HITWDQLWMLMA (SEQ ID NO 74) |
| GSDSHITWDELWNLMNPVLA (SEQ ID NO 75) | |
| NWLDDITWDELWKIMNPSTA (SEQ ID NO 76) | |
| ETDDHITWDQLWRIMTATMA (SEQ ID NO 77) | |
| WTDTHITWDQLWHFMNMGEQ (SEQ ID NO 78) | |

TABLE 1-continued

```
                GFGEAITWDQLWDMMNGEDA (SEQ ID NO 79)
                NVAEQITWDQLWNLMSVGSS (SEQ ID NO 80)
                GQTGLITWDMLWNLMNPVGE (SEQ ID NO 81)
                GTGDHITWDQLWNLMINEKG (SEQ ID NO 82)
                EYGRHITWDQLWQLMQSATA (SEQ ID NO 83)
                MNNWHVSWEQLWDIMNGPPN (SEQ ID NO 84)
                ESASHITWGQLWDLMNASEV (SEQ ID NO 85)
                YWRGNITWDQLWNIMNSEYS (SEQ ID NO 86)
                AGASHITWAQLWNMMNGNEG (SEQ ID NO 87)
                GSWAHITWDQLWNLMNMGTQ (SEQ ID NO 88)
                YGNSNITWDQLWSIMNRQTT (SEQ ID NO 89)
                AHLPHISWDTLWHIMNKGEK (SEQ ID NO 90)
                ESASHITWGQLWDLMNASEV (SEQ ID NO 91)
                MNNWHVSWEQLWDIMNGPPN (SEQ ID NO 92)
                GFGEAITWDQLWDMMNGEDA (SEQ ID NO 93)
                WTDTHITWDQLWHFMNMGEQ (SEQ ID NO 94)
EMTWAELWTLME (SEQ ID NO 95)        DYTWFELWDMMQ (SEQ ID NO 5)
DYSWHDLWEMMS (SEQ ID NO 8)         DISWRQLWDIMN (SEQ ID NO 96)
EISWLGLWDIMN (SEQ ID NO 97)        DMTWHDLWTLMS (SEQ ID NO 98)
RGVWGGLWSMTW (SEQ ID NO 99)        EMTWQQLWVVMQ (SEQ ID NO 100)
                AEWTWDQLWHVMNPAESQ (SEQ ID NO 101)
                RNMSWLELWEHMK (SEQ ID NO 102)
                SQVTWNDLWSVMNPEVVN (SEQ ID NO 103)
                HRAEWLALWEQMSP (SEQ ID NO 104)
                YKKEWLELWHQMQA (SEQ ID NO 105)
                RSLSWLQLWDQMK (SEQ ID NO 106)
                KEQQWRNLWKMMS (SEQ ID NO 107)
                KKEDWLALWRIMSVPD (SEQ ID NO 108)
                RNMSWLELWEHMK (SEQ ID NO 109)
                GRPTWNELWDMMQAP (SEQ ID NO 110)
                KRKQWIELWNIMS (SEQ ID NO 111)
                KTSEWNNLWKLMSQ (SEQ ID NO 112)
```

The norleucine derivatives, in which the conserved M is replaced with Nle, are especially noteworthy, as these derivatives may be more stable under certain environmental conditions than other peptides of the invention that contain an M at this position. Examples of such preferred peptides wherein M is replaced by Nle are as follows:

DITWDQLWDLNleK (SEQ ID NO 9)
DGDITWDQLWDLNleK (SEQ ID NO 113)
QITWDQLWDLNleK (SEQ ID NO 115)
AITWDQLWDLNleK-OH (SEQ ID NO 134)
DATWDQLWDLNleK-OH (SEQ ID NO 135)
DITADQLWDLNleK-OH (SEQ ID NO 136)
DITWAQLWDLNleK-OH (SEQ ID NO 137)
DITWDALWDLNleK-OH (SEQ ID NO 138)
DITWDQAWDLNleK-OH (SEQ ID NO 139)
DITWDQLADLNleK-OH (SEQ ID NO 140)
DITWDQLWALNleK-OH (SEQ ID NO 141)
DITWDQLWDANleK-OH (SEQ ID NO 142)
DITWDQLWDLAK-OH (SEQ ID NO 143)
DITWDQLWDLNleA-OH (SEQ ID NO 144)
Ac-DITWDQLWDLNleK-NH$_2$ (SEQ ID NO 158)

Peptides and peptide mimetics having an $IC_{50}$-HL60 of greater than about 100 μM lack sufficient binding to permit use in either the diagnostic or therapeutic aspects of this invention. Preferably, for diagnostic purposes, the peptides and peptide mimetics have an $IC_{50}$-standard of about 2.5 mM or less and, for pharmaceutical purposes, the peptides and peptide mimetics have and $IC_{50}$-standard of about 2 mM or less.

Figure 4:
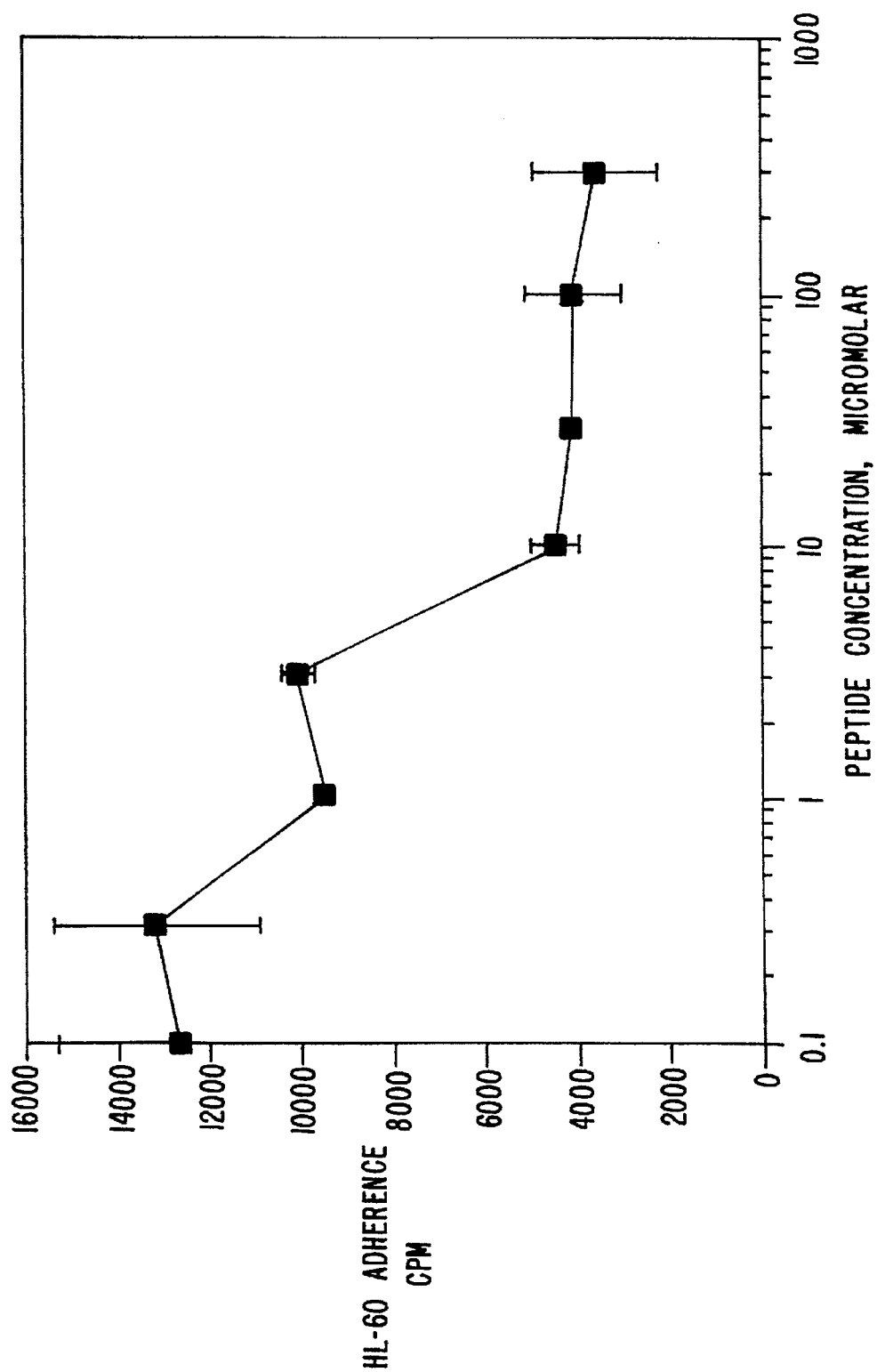
FIG. 4 illustrates the results of a cell adhesion assay in the presence of a preferred peptide of the invention, DITWDQLWDLMK (SEQ ID NO 3).

The binding peptide sequence also provides a means to determine the minimum size of an E-selectin binding, cell adhesion blocking compound of the invention. Several deletion analogs of a lead peptide of the invention are shown in FIG. 4; one preferred peptide is ITWDQLWDLMK SEQ ID NO 160). Using the "very large scale immobilized polymer synthesis" system described in U.S. Pat. No. 5,143,845 and related publications, supra, one not only can determine the minimum size of a peptide with E-selectin binding activity, but also can make all of the peptides that form the group of peptides that differ from the lead compound in one, two, or more residues, or that differ in containing non-natural amino acids. This collection of peptides and peptide mimetics can then be screened for ability to bind to E-selectin. This immobilized polymer synthesis system or other peptide synthesis methods, such as the ESL method discussed above, can also be used to synthesize every truncation, deletion, and every combination of truncation and deletion analogs of the peptide compounds of the invention.

Random peptide synthesis can also be employed to generate a multiplicity of other peptides of varying length which can be used in the assay methods described herein to determine E-selectin binding. Once peptides which bind E-selectin are determined, these peptides can be used as "lead peptides" in the manner described above to obtain peptides having enhanced E-selectin binding.

Additionally, the following peptides were identified by the random peptide diversity generation systems described above with the exception that the expression was on pVIII instead of pIII for identification purposes. Several of these peptides were actually found in a pIII mutagenesis library but others (SEQ ID NOS 11–15) were found only on pVIII.

YDDVCCELLF (SEQ ID NO 11)
DLPQWYTEWC (SEQ ID NO 12)
ENSHWCTCPC (SEQ ID NO 13)
DIEQDWVTWM (SEQ ID NO 14)
NEWCVVPCRL (SEQ ID NO 15)
DIWQDWVRWM (SEQ ID NO 16)
DLWQDWVTWM (SEQ ID NO 17)
DLWQDWVHWM (SEQ ID NO 18)

DIWQDWVTWM (SEQ ID NO 19)
DIWQDWVKWM (SEQ ID NO 20)
DIWQDWVRWM-NH$_2$ (SEQ ID 16)
DIWEDWVRWM (SEQ ID 21)
DIWQDWITWM (SEQ ID 22)

The simple in vitro assays set forth above and in the examples hereinbelow provide a straightforward method for preparing and screening peptides and peptide mimetics for their binding properties to E-selectin.

B. Preparation of Peptides and Peptide Mimetics Which Bind E-Selectin

Peptides

The peptides identified above as binding E-selectin can also be prepared by classical methods known in the art including standard solid phase techniques. The standard methods include exclusive solid phase synthesis, partial solid phase synthesis, fragment condensation, classical solution synthesis, and recombinant DNA technology. See, e.g., Merrifield[35]. On solid phase, the synthesis is typically commenced from the C-terminal end of the peptide using an α-amino protected resin. A suitable starting material can be prepared, for instance, by attaching the required α-amino acid to a chloromethylated resin, a hydroxymethyl resin, or a benzhydrylamine resin. One such chloromethylated resin is sold under the tradename BIO-BEADS SX-1 by BioRad Laboratories, Richmond, Calif., USA, and the preparation of the hydroxymethyl resin is described by Bodonszky, et al.[36] The benzhydrylamine (BHA) resin has been described by Pietta and Marshall[37], and is commercially available from Beckman Instruments, Inc., Palo Alto, Calif., USA, in the hydrochloride form. A particularly preferred resin is a PAL resin available from Millipore Corp., Bedford, Mass., USA.

Thus, the compounds of the invention can be prepared by coupling an α-amino protected amino acid to the chloromethylated resin with the aid of, for example, cesium bicarbonate catalyst, according to the method described by Gisin[38]. After the initial coupling, the α-amino protecting group is removed by a choice of reagents including trifluoroacetic acid (TFA) or hydrochloric acid (HCl) solutions in organic solvents at room temperature.

The α-amino protecting groups are those known to be useful in the art of stepwise synthesis of peptides. Included are acyl type protecting groups (e.g. formyl, trifluoroacetyl, acetyl), aromatic urethane type protecting groups (e.g. benzyloxycarboyl (Cbz) and substituted Cbz), aliphatic urethane protecting groups (e.g. t-butyloxycarbonyl (Boc), isopropyloxycarbonyl, cyclohexyloxycarbonyl, 9-fluorenylmethoxycarbonyl (F-moc) and alkyl type protecting groups (e.g. benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, 2-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Thr and Ser is benzyl. The side chain protecting groups for Arg include nitro, tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl -Cbz), 2-bromobenzyloxycarbonyl (2-Br-Cbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide can be decoupled from the resin support by treatment with a reagent such as hydrogen fluoride (HF) or trifluoroacetic acid (TFA), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide (i.e., the C-terminus is —$C(O)NH_2$). Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide (i.e., the C-terminus is —$C(O)NR^3R^4$ where $R^3$ and $R^4$ are as defined above). Side chain protection is then removed in the usual fashion by treatment with hydrogen fluoride to give the free amides, alkylamides, or dialkylamides.

These solid phase peptide synthesis procedures are well known in the art and further described in Stewart[40].

The amino acids employed in the above described methods for peptide synthesis can either be naturally occurring amino acids or synthetic amino acids other than the 20 naturally occurring, genetically encoded amino acids. For instance, naphthylalanine can be substituted for tryptophan, facilitating synthesis. Other synthetic amino acids that can be substituted into the peptides of the present invention include L-hydroxypropylglycine, L-3,4-dihydroxyphenylalanyl, α-amino acids such as L-α-hydroxylysyl and D-α-methylalanyl, L-α-methyl-alanyl, β amino-acids such as β-analine, and isoquinolyl.

D-amino acids and other non-naturally occurring synthetic amino acids can also be incorporated into the peptides of the present invention. Such other non-naturally occurring synthetic amino acids include those where the naturally occurring side chains of the 20 genetically encoded amino acids (or any L or D amino acid) are replaced with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4, 6, or 7 members can be employed.

Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides which bind E-selectin by phosphorylation, and other methods for making peptide derivatives of the compounds of the present invention are described in Hruby et al.[42] Thus, the peptide compounds of the invention also serve as a basis to prepare peptide mimetics with similar biological activity.

Peptide Mimetics

Those of skill in the art recognize that a variety of techniques are available for constructing peptide mimetics with the same or similar desired biological activity as the corresponding peptide compound but with more favorable activity than the peptide with respect to solubility, stability, and susceptibility to hydrolysis and proteolysis. See, for example, Morgan and Gainor[41]. The following describes methods for preparing peptide mimetics modified at the N-terminal amino group, the C-terminal carboxyl group, and/or changing one or more of the amido linkages in the peptide to a non-amido linkage. It being understood that two or more such modifications can be coupled in one peptide mimetic structure (e.g., modification at the C-terminal carboxyl group and inclusion of a —$CH_2$-carbamate linkage between two amino acids in the peptide).

Modification of the N-amino Terminus

After the desired amino acid sequence has been completed as described above, the blocking group on the N-terminus amino group can be selectively removed so as to provide for a peptide sequence blocked at all positions other than the N-terminal amino group and attached to a solid resin through the C-terminus. One can then modify the amino terminus of the peptides of the invention to produce peptide mimetics of the invention.

Amino terminus modifications are as recited above and include alkylating, acetylating, adding a carbobenzoyl group, forming a succinimide group, etc. Specifically, the N-terminal amino group can then be reacted as follows:

(a) to form an amide group of the formula RC(O)NH— where R is as defined above by reaction with an acid halide [e.g., RC(O)Cl] or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (e.g., about 5 equivalents) can be employed and the amino group is converted to the succinimide by methods well known in the art including the use of an excess (e.g., ten equivalents) of a tertiary amine such as diisopropylethylamine in a suitable inert solvent (e.g., dichloromethane). See, for example, Wollenberg, et al., U.S. Pat. No. 4,612,132 which is incorporated herein by reference in its entirety. It is understood that the succinic group can be substituted with, for example, $C_2$-$C_6$ alkyl or —SR substituents which are prepared in a conventional manner to provide for substituted succinimide at the N-terminus of the peptide. Such alkyl substituents are prepared by reaction of a lower olefin ($C_2$-$C_6$) with maleic anhydride in the manner described by Wollenberg, et al., supra. and —SR substituents are prepared by reaction of RSH with maleic anhydride where R is as defined above;

(c) to form a benzyloxycarbonyl-NH— or a substituted benzyloxycarbonyl-NH— group by reaction with approximately an equivalent amount or an excess of CBZ-Cl (i.e., benzyloxycarbonyl chloride) or a substituted CBZ-Cl in a suitable inert diluent (e.g., dichloromethane) preferably containing a tertiary amine to scavenge the acid generated during the reaction;

(d) to form a sulfonamide group by reaction with an equivalent amount or an excess (e.g., 5 equivalents) of R—$S(O)_2$Cl in a suitable inert diluent (dichloromethane) to convert the terminal amine into a sulfonamide where R is as defined above. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes);

(e) to form a carbamate group by reaction with an equivalent amount or an excess (e.g., 5 equivalents) of R—OC(O)Cl or R—OC(O)O$C_6H_4$—p—$NO_2$ in a suitable inert diluent (e.g., dichloromethane) to convert the terminal amine into a carbamate where R is as defined above. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes); and (f) to form a urea group by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

As shown in the examples below, peptides having modifications to the N-terminus amino group provide for peptide mimetics having binding properties to E-selectin as determined by an $IC_{50}$-standard of less than 2.5 mM.

Modification of the C-Terminus

In preparing peptide mimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester.

In preparing peptide mimetics wherein the C-terminal carboxyl group is replaced by the amide —C(O)N$R^3R^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

As shown in the examples below, peptides having modifications to the C-terminal carboxyl group provide for peptide mimetics having binding properties to E-selectin as determined by an IC$_{50}$-standard of less than 2.5 mM.

Modification to Incorporate a Non-Peptidyl Linkage

Peptide mimetics wherein one or more of the peptidyl linkages [—C(O)NH—] have been replaced by such linkages as a —CH$_2$-carbamate linkage, a phosphonate linkage, a —CH$_2$-sulfonamide linkage, a urea linkage, a secondary amine (—C$_2$NH—) linkage, and an alkylated peptidyl linkage [—C(O)NR$^6$— where R$^6$ is lower alkyl] are prepared during conventional peptide synthesis by merely substituting a suitably protected amino acid analogue for the amino acid reagent at the appropriate point during synthesis.

Suitable reagents include, for example, amino acid analogues wherein the carboxyl group of the amino acid has been replaced with a moiety suitable for forming one of the above linkages. For example, if one desires to replace a —C(O)NR— linkage in the peptide with a —CH$_2$-carbamate linkage (—CH$_2$OC(O)NR—), then the carboxyl (—COOH) group of a suitably protected amino acid is first reduced to the —CH$_2$OH group which is then converted by conventional methods to a —OC(O)Cl functionality or a para-nitrocarbonate —OC(O)O—C$_6$H$_4$—p—NO$_2$ functionality. Reaction of either of such functional groups with the free amine or an alkylated amine on the N-terminus of the partially fabricated peptide found on the solid support leads to the formation of a —CH$_2$OC(O)NR— linkage. For a more detailed description of the formation of such —CH$_2$-carbamate linkages, see Cho, et al.[39]

Similarly, replacement of an amido linkage in the peptide with a phosphonate linkage can be achieved in the manner set forth in U.S. patent application Ser. Nos. 07/943,805, 08/081,577, and 08/119,700, the disclosures of which are incorporated herein by reference in their entirety.

Replacement of an amido linkage in the peptide with a —CH$_2$-sulfonamide linkage can be achieved by reducing the carboxyl (—COOH) group of a suitably protected amino acid to the —CH$_2$OH group and the hydroxyl group is then converted to a suitable leaving group such as a tosyl group by conventional methods. Reaction of the tosylated derivative with, for example, thioacetic acid followed by hydrolysis and oxidative chlorination will provide for the —CH$_2$—S(O)$_2$Cl functional group which replaces the carboxyl group of the otherwise suitably protected amino acid. Use of this suitably protected amino acid analogue in peptide synthesis provides for inclusion of an —CH$_2$S(O)$_2$NR— linkage which replaces the amido linkage in the peptide thereby providing a peptide mimetic. For a more complete description on the conversion of the carboxyl group of the amino acid to a —CH$_2$S(O)$_2$Cl group, see, for example, *Chemistry & Biochemistry of Amino Acids, Peptides and Proteins*, Edited by Boris Weinstein, Vol. 7, pp. 267–357, Marcel Dekker, Inc., New York, N.Y. (1983) which is incorporated herein by reference in its entirety.

Replacement of an amido linkage in the peptide with a urea linkage can be achieved in the manner set forth in U.S. patent application Ser. No. 08/147,805 which application is incorporated herein by reference in its entirety.

Secondary amine linkages wherein a —CH$_2$NH— linkage replaces the amido linkage in the peptide can be prepared by employing, for example, a suitably protected dipeptide analogue wherein the carbonyl bond of the amido linkage has been reduced to a CH$_2$ group by conventional methods. For example, in the case of diglycine, reduction of the amide to the amine will yield after deprotection H$_2$NCH$_2$CH$_2$NHCH$_2$COOH which is then used in N-protected form in the next coupling reaction. The preparation of such analogues by reduction of the carbonyl group of the amido linkage in the dipeptide is well known in the art.

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10 fold excess. The reaction results in incorporation into the peptide mimetic of an amino acid analogue having a non-peptidyl linkage. Such substitution can be repeated as desired such that from zero to all of the amido bonds in the peptide have been replaced by non-amido bonds.

Utility

The peptides and peptide mimetics of the invention are useful in vitro as unique tools for understanding the biological role of E-selectin, as well as other receptors of the selectin family, such as CD62, that may bind to the peptide compounds of the invention. The peptides and peptide mimetics of the invention can also be used to evaluate the many factors thought to influence, and be influenced by, the cell adhesion process. The present compounds are also useful in the development of other compounds that bind to E-selectin, because the present compounds provide important SAR information that facilitate that development.

The peptides and peptide mimetics of this invention can also be labeled with a detectable label and used to diagnose the in vivo site(s) of inflammation. When used for this purpose, a suitable detectable label is covalently attached to a peptide or peptide mimetic of this invention and an effective amount of the so-labeled peptide or peptide mimetic is administered to the patient. Sufficient time after administration is allowed to pass so as to permit circulation of the labeled peptide or peptide mimetic in the patient and attachment to the site of E-selectin expression. At this point, detection of the label and its location in the patient is determined so as to provide for the site of inflammation.

The peptides and peptide mimetics of this invention can also be employed to target conventional anti-inflammatory drugs or other agents to specific sites of tissue injury. By using an E-selectin binding peptide or peptide mimetic of this invention to target such a drug to the E-selectin receptor on, e.g., a vascular endothelial cell, such drug/peptide composites can achieve higher drug concentrations at the sites of injury. Side effects from the conventional administration of anti-inflammatory drugs can be reduced by the lower dosages of drug required and the localization of the drug at the site of injury.

Preferably, the anti-inflammatory drug is coupled to the peptide or peptide mimetic of this invention via covalent linkages and is conducted in a manner such the coupling does not substantially inhibit the ability of the peptide or peptide mimetic from binding to E-selectin. A variety of anti-inflammatory agents can be coupled for targetting in this manner including, by way of example, cyclosporin A, indomethacin, naproxen, FK-506, mycophenolic acid, etc.

The peptides and peptide mimetics of the invention can also be administered to warm blooded animals, including humans, to treat conditions mediated by E-selectin expression in vivo. Thus, the present invention encompasses methods for therapeutic treatment of E-selectin related disorders, especially inflammatory disorders, that comprise administering a peptide or peptide mimetic of the invention in amounts sufficient to block the adhesion of leukocytes to E-selectin in vivo. For example, the peptides and compounds of the invention can be administered to control inflammatory conditions and other conditions mediated by E-selectin. Such inflammatory conditions mediated by selectin proteins include, by way of example, (1) dermal inflammation, including Il-1-induced skin inflammation; atopic dermatitis, psoriasis, and allergic contact dermatitis; delayed-type hypersensitivity reaction; and endotoxin-induced acute cutaneous inflammation in baboons; (2) intestinal inflammation, including inflamed colonic mucosa of patients with ulcerative or Crohn's colitis; inflammatory bowel disease; and intestinal graft-versus-host disease; (3) other sites of inflammation, including synovial tissues from patients with rheumatoid arthritis and osteo arthritis; rat endotoxin-induced uveitis, and inflamed endothelium of asthma model (primate antigen inhalation), acute respiratory distress syndome (ARDS); (4) septic shock, and (5) and the overproduction of cytokines that stimulate expression of E-selectin, or other members of the selectin family.

In addition to the above human uses, it is contemplated that these peptides can be used in veterinary uses due to cross-reactivity with the selectins expressed in the particular animal.

Accordingly, the present invention includes pharmaceutical compositions comprising, as an active ingredient, at least one of the peptides or peptide mimetics of the invention in association with a pharmaceutical carrier or diluent. The peptides and peptide mimetics of this invention are effective in treating E-selectin mediated conditions when administered at a dosage range of from about 0.001 mg to about 20 mg/kg of body weight per day. The specific dose employed is regulated by the particular condition being treated, the route of administration as well as by the judgement of the attending clinician depending upon factors such as the severity of the condition, the age and general condition of the patient, and the like.

The peptide and peptide mimetics of the invention can be administered by oral, parenteral (intramuscular, intraperitoneal, intravenous (IV) or subcutaneous injection), transdermal, nasal, vaginal, rectal, pulmonary, sublingual or inhalation (via a fine powder formulation) routes of administration and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

As can be appreciated from the disclosure above, the present invention has a wide variety of applications. Accordingly, the following examples are offered by way of illustration, not by way of limitation.

In the examples below, the following abbreviations have the following meanings. If not defined below, then the abbreviations have their art recognized meanings.

| | | |
|---|---|---|
| BSA | = | bovine serum albumin |
| DMEM | = | Dulbecco's modified eagle medium |
| DMSO | = | dimethylsulfoxide |
| ELAM-1 | = | endothelial leukocyte adhesion molecule-1 |
| FCS | = | fetal calf serum |
| F-moc | = | 9-fluorenyl-methoxycarbonyl |

-continued

| | | |
|---|---|---|
| F12 | = | F-12 nutrient mixture available from Gibco |
| HEPES | = | N-2-hydroxyethylpiperazine-N'-2-ethanesulfonic acid |
| mL | = | milliliter |
| mM | = | millimolar |
| nM | = | nanomolar |
| PBS | = | phosphate buffered saline |
| RPM | = | rotations per minute |
| SLe$^x$ | = | sialyl Lewis$^x$, i.e., αNeu5Ac(2→3)-Gal(1→4)-[α-L-Fuc(1→3)]-βGlcNAc- |
| μCi | = | microCurie |
| μg | = | micrograms |
| μL | = | microliters |
| μM | = | micromolar |

EXAMPLE 1

HL60 Cell Adhesion Assay

This example describes the results of a cell adhesion assay in which the ability of HL60 cells (a promyelocytic leukemia-60 cell clone that expresses Sle$^x$ and is available from the ATCC (Rockville, Md.) as ATCC No. CCL 240) to adhere to immobilized E-selectin was tested in the presence of various compounds, including an E-selectin binding peptide of the invention.

The assay requires HL60 cells labeled with tritiated thymidine. To label the cells, about 10 million HL60 cells are collected by centrifugation (2500 RPM for 3 minutes) and resuspended in 15 mL of DMEM/F12 plus 5% fetal calf serum containing 2 μCi/mL of tritiated thymidine (Amersham). The cells are then placed in a T75 flask and incubated at 37° C. for 24 hours. The cells are then collected by centrifugation, washed twice with RPMI/HEPES/0.1% FCS, and resuspended in the same solution at a concentration of about one to two million cells per mL. About 100 μL of this cell preparation are used per well of a 96-well microtiter dish in the assay.

The wells of the microtiter dish were first coated with the anti-receptor immobilizing antibody, an anti-HPAP-tail antibody, using about 2.5 μg of antibody per well. The wells were then treated with a solution composed of 1% BSA in PBS and then with a 1:10 dilution (1:100 and 1:500 dilutions and immobilizations were also conducted and tested) of a soluble E-selectin harvest (the E-selectin harvest, prepared by treating cells expressing PIG-tailed E-selectin with phospholipase C and collecting the resulting solution, was diluted in a solution composed of RPMI, HEPES, 0.1% BSA, and 0.1% sodium azide). All compounds tested were added prior to the addition Of the labeled HL60 cells and allowed to incubate at 4° C. for one hour.

After the test compound incubation period, 100 μL of labeled HL60 cells were added to each well, and the microtiter plate was incubated at 4° C. for 30 minutes. Then, the wells were washed three times with RPMI 1640 plus 0.1% FCS using a multichannel pipettor. After the wells were washed, 100 μL of 0.1 N NaOH were added to each well, and the microtiter plate was incubated at room temperature for 10 minutes. After this incubation, aliquots were removed from each well and placed in scintillation vials; scintillation fluid was added to each vial; and the radioactivity in each aliquot was quantitated by liquid scintillation counting.

The compounds tested were as follows: (1) "BBA-2" is an E-selectin blocking antibody purchased from R&D Systems, 614 McKinley Place NE, Minneapolis, Minn. 55413 as product code BBG57 and used at a concentration of about 200 nM; (2) "anti 176" is an antibody that does not bind to the E-selectin used at a concentration of about 200 nM as a negative control; (3) "AFFY 4" is peptide HITWDQLWN-VMN (SEQ ID NO 23), with a free amino and a free carboxy terminus, used at a concentration of 200 μM after dissolving in DMSO and diluting in PBS/DMSO to a final concentration of 5% DMSO; (4) "AFFY 1" is an unrelated peptide used at a concentration of about 200 μM as a negative control; and (5) a "SLe$^x$" derivative, monofucosyl monosialyllactose at a concentration of about 200 μM. The results of the assay are presented in FIG. 1, which reflects HL60 cell binding as a percent of the binding observed in the absence of any added compound.

Figure 2A:
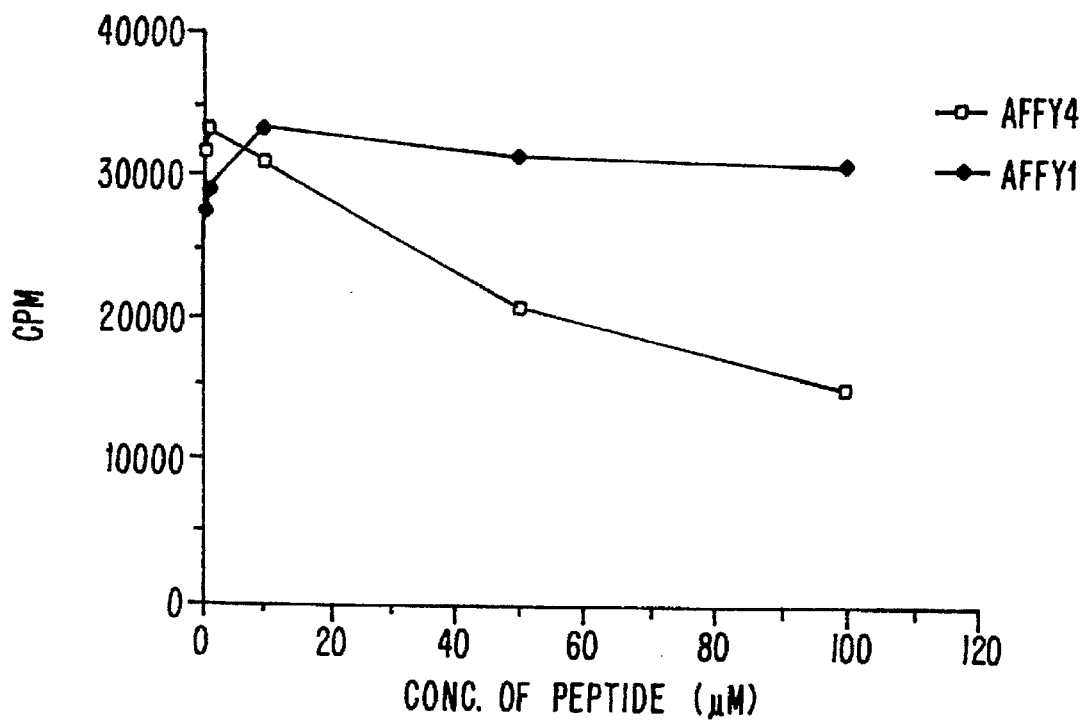
FIG. 2A illustrates the results of a cell adhesion assay in the presence of various concentrations of an E-selectin blocking peptide of the invention; the assay is described in Example 1
Figure 2B:
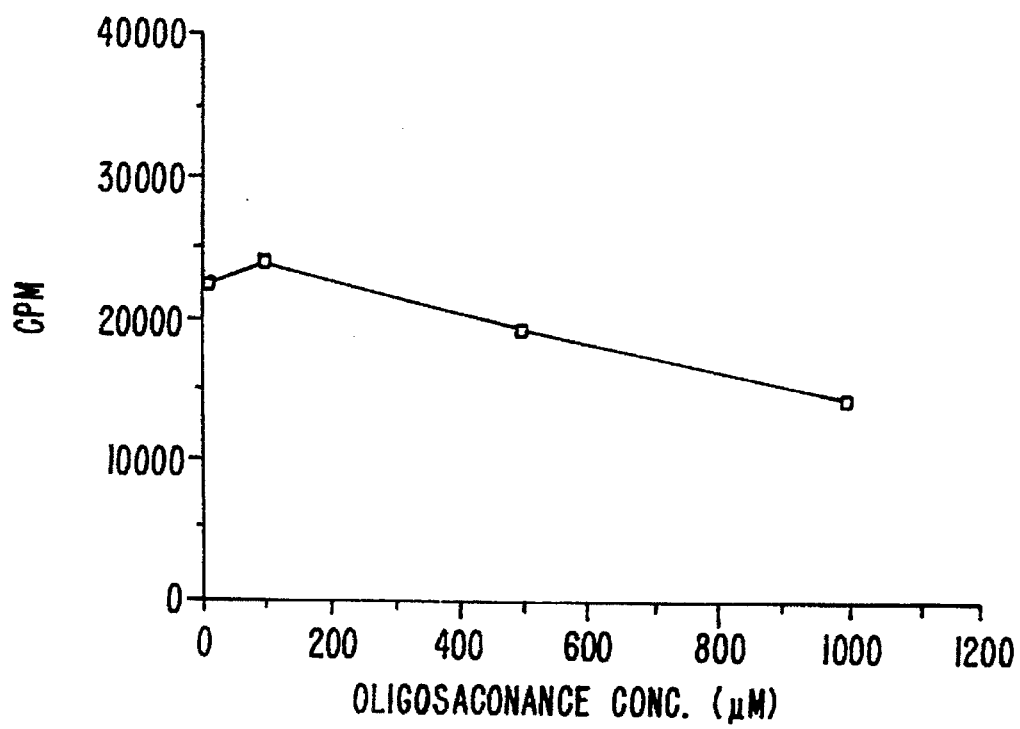
FIG. 2B illustrates the results of the same assay in varying concentrations of a monofucosyl monosialyllactose.

As shown in FIG. 1, the peptide HITWDQLWNVMN (SEQ ID NO 23) blocked over 80% of the cell binding that occurred in the absence of added compound. This result compares favorably with the blocking observed in the presence of BBA-2 (about 65%). The negative controls (anti 176 and AFFY 1) showed no significant blocking of HL60 binding. Although SLe$^x$ did not exhibit significant blocking of cell adhesion at the concentration used in this assay, subsequent experiments showed that SLe$^x$ does block cell adhesion if used at a concentration of 500 to 1000 μM as illustrated in FIG. 2B.

The concentration of any peptide or peptide mimetic required to reduce by 50% the binding of HL60 cells to E-selectin as per the assay of Example 1 is determined by the following procedure. In this procedure the IC$_{50}$-HL60 of a specific peptide, HITWDQLWNVMN (SEQ ID NO 23), was determined. It being understood that the procedure employed can be used to the determine the IC$_{50}$-HL60 of other peptides and peptide mimetics.

The peptide HITWDQLWNVMN (SEQ ID NO 23) was tested in the cell adhesion assay at varying concentrations (from 0.5 to 100 μM) along with a negative control (the AFFY 1 peptide). The results of this assay, plotted as cpm observed against peptide concentration, are shown in FIG. 2A. From this figure, the concentration of the peptide HITWDQLWNVMN (SEQ ID NO 23) required to inhibit binding of HL60 cells by about 50% is determined to be about 50 μM and this value is taken as the IC$_{50}$-HL60 value for this peptide.

FIG. 4 graphically illustrates the IC$_{50}$-HL60 for a second peptide DITWDQLWDLMK (SEQ ID NO 3) which has an IC$_{50}$-HL60 of less than about 10 μM.

The above results demonstrate that this simple in vitro assay provides a facile means to determine the binding affinity of a candidate peptide or peptide mimetic to E-selectin as measured by its IC$_{50}$-HL60.

Figure 3A:
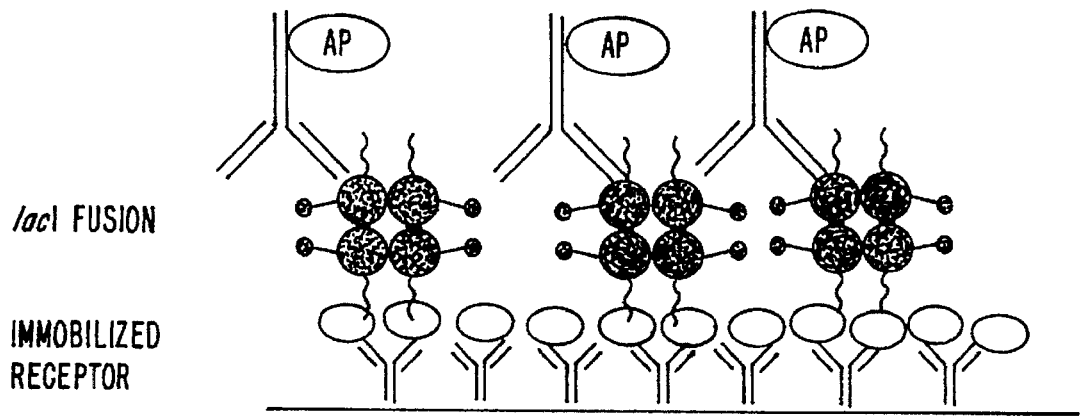
FIGS. 3A and 3B illustrate two peptides on plasmids assay formats.
Figure 3B:
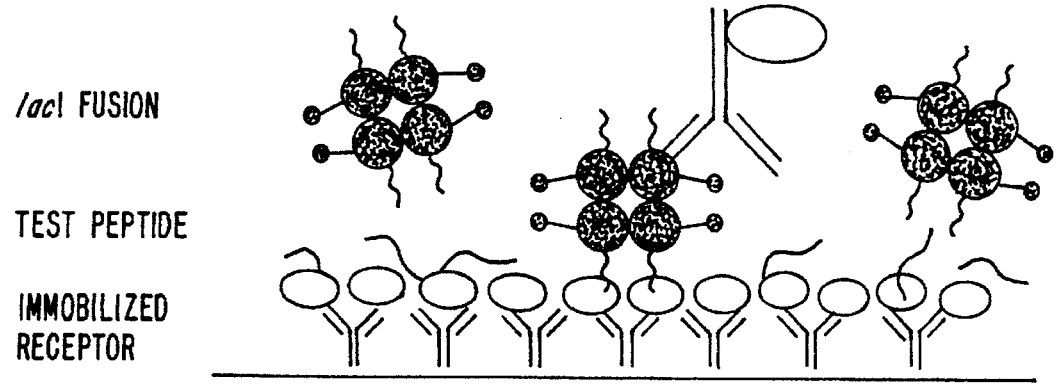

FIGS. 3A and 3B illustrate two assay formats for peptides of the invention the second of which is exemplified in detail in Example 2 which follows.

EXAMPLE 2

DETERMINATION OF THE IC$_{50}$-STANDARD FOR DIFFERENT PEPTIDES AND PEPTIDE MIMETICS

This example measures the concentration of peptide or peptide mimetic required to inhibit 50% of the binding of a radiolabeled standard to E-selectin and the resulting IC$_{50}$ value is referred to as the "IC$_{50}$-standard". In this example, the standard corresponds to the synthetic peptide LRRASLGDGDITWDQLWDLMK (SEQ ID NO 114) which comprises a known initial seven amino acid group which is a substrate for protein kinase A followed by a 2 amino acid spacer and a 12 amino acid sequence which corresponds to the peptide identified by SEQ ID NO 3 which has an $IC_{50}$-HL60 of 10 μM. The peptide is radiolabeled by phosphorylation using either $^{33}$p or $^{33}$P phosphate by conventional methods via the protein kinase A. The example is a competitive assay in which 6.5 picograms at 1400 Ci/mmol (65000 cpm) of radiolabelled standard (1400 Ci/mmol) is combined with a titered amount of candidate peptide or peptide mimetic in a constant volume of 30 μL. The combined solution is then added to E-selectin immobilized onto a solid surface in the manner described above. The resulting mixture is then incubated for about 120 minutes to permit equilibrium binding to be achieved. Afterwards, unbound materials are separated from bound materials by conventional methods (e.g., washing) and the amount of the candidate peptide or peptide mimetic bound to E-selectin is determined by scintillation counting. The assay is repeated over several concentrations of candidate peptide or peptide mimetic and the results are entered into a graph whose y axis is the amount of radiolabeled standard bound to E-selectin (measured in cpm) and the x axis is the amount of candidate peptide or peptide mimetic. The results are graphically extrapolated to determine the concentration at which the peptide or peptide mimetic will reduce by 50% the amount of radiolabeled standard bound to E-selectin. This concentration is taken as the $IC_{50}$-standard for that peptide or peptide mimetic.

Additional peptides were prepared synthetically as free peptides and assayed in the manner described above to determine their $IC_{50}$-standard values. The results of this assay are shown in the following table:

| PEPTIDE SEQUENCE | $IC_{50}$-STANDARD |
|---|---|
| DITWDQLWDLMK (SEQ ID NO 3) | 3 nM |
| DGDITWDQLWDLMK (SEQ ID NO 4) | 4 nM |
| DYTWFELWDMMQ (SEQ ID NO 5) | 6 nM |
| DITWDELWKIMN (SEQ ID NO 6) | 7 nM |
| QITWAQLWNMMK (SEQ ID NO 7) | 12 nM |
| DYSWHDLWEMMS (SEQ ID NO 8) | 16 nM |
| DITWDQLWDLNleK (SEQ ID NO 9) | 23 nM |
| HITWDQLWRIMT (SEQ ID NO 10) | 28 nM |
| RNMSWLELWEHMK (SEQ ID NO 102) | 35 nM |
| DGDITWDQLWDLNleK (SEQ ID NO 113) | 42 nM |
| QITWDQLWDLNleK (SEQ ID NO 115) | 65 nM |
| AEKWDQLWHVMNPAESQ (SEQ ID NO 116) | 65 nM |
| DITWAQLWNNleNleN (SEQ ID No 117) | 425 nM |
| d-DITWDQLWDLMK | 25 nM |
| Dd-ITWDQLWDLMK | 27 nM |
| DId-TWDQLWDLMK | 2700 nM |
| DITWd-DQLWDLMK | 34 nM |
| DITWDQLWDd-LMK | 33000 nM |
| DITWDQLWDLMd-K | 1000 nM |
| DITWDQLWDLMK-CONH$_2$ (SEQ ID NO 166) | 22 nM |
| ITWDQLWDLMK (SEQ ID N0 160) | 11 nm |
| TWDQLWDLMK (SEQ ID NO 162) | 12 μM |

As shown above, a number of the peptides have $IC_{50}$-standard values of about 10 nanomolar (nM) or less.

EXAMPLE 3

BINDING OF PEPTIDES TO SELECTINS OTHER THAN E-SELECTIN

This example demonstrates that certain of the peptides of this invention also have binding affinity for selectins other than E-selectin including the P-selectin and the L-selectin. In this example, the binding specificity of certain peptides on phage for the E-selectin, the P-selectin, the L-selectin and NGF R (control) were conducted using an ELISA procedure to determine if the peptides bind specifically to these selectins. This assay was carried out similarly to the procedures used in the affinity enrichment process described above, except that after removing unbound phage from the wells, the wells were treated with rabbit anti-phage antibody, then with alkaline phosphatase (AP)-conjugated goat anti-rabbit immunoglobulin antibody, or with anti-LacI-AP, as shown in FIG. 3, part A, and then the amount of alkaline phosphatase in each well was determined measuring the optical density at 405 nm. The amount of alkaline phosphatase in each well is determined by incubation of a chromogenic enzyme substrate with the material left in the well. If cleaved by the enzyme, a color is produced. If no enzyme is present, no color appears; this is interpreted to mean that no goat anti-rabbit Ig/AP was bound.

Figure 5:
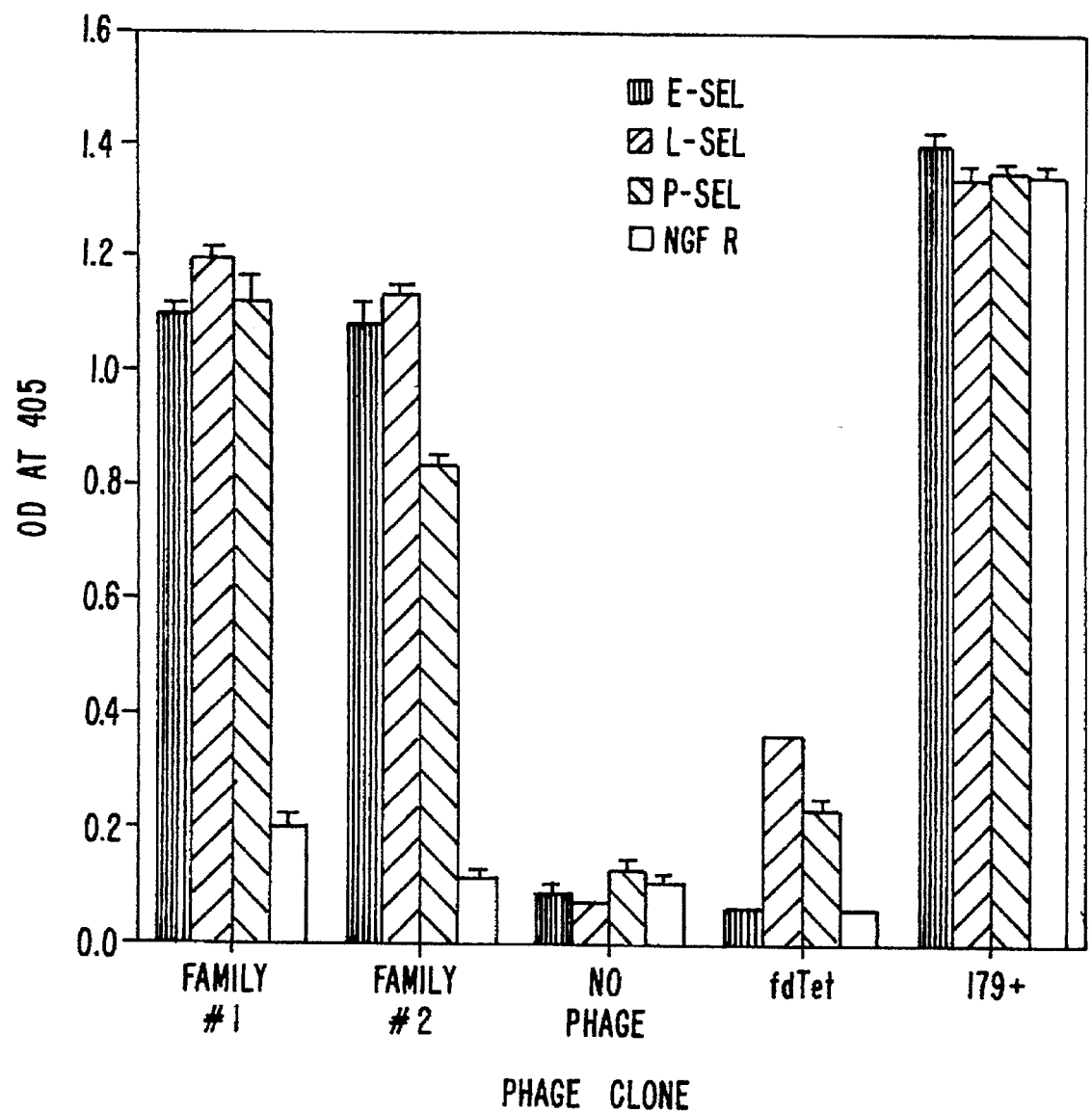
FIG. 5 illustrates that certain peptides having high binding specificity for E-selectin can also bind other selectins such as P-selectin and L-selectin.

The results of this analysis are set forth in FIG. 5 wherein peptides from families 1 and 2 clearly show binding affinity for each of the selectins as compared to control.

EXAMPLE 4

BINDING OF PEPTIDES CONTAINING SYNTHETIC AMINO ACIDS TO E-SELECTIN

This example demonstrates that peptide containing synthetic amino acids can bind to the E-selectin. Specifically, in this example, the following synthetic amino acids were employed:

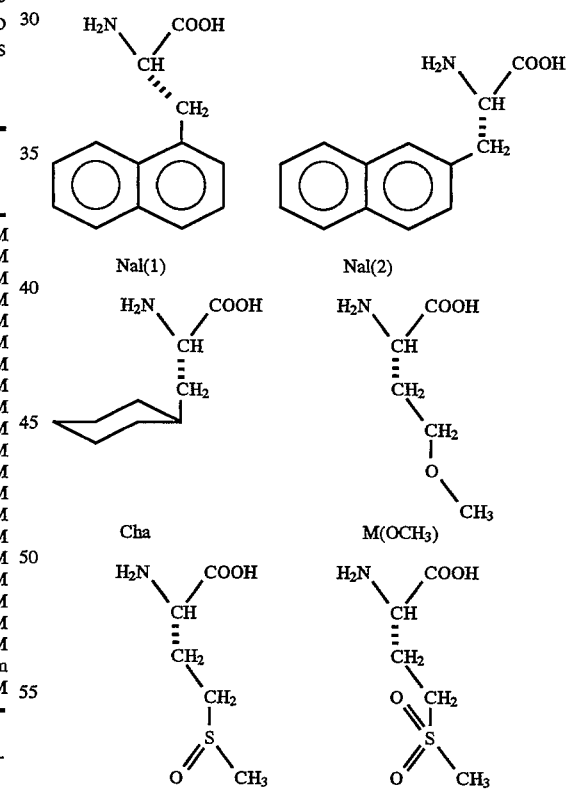

and 2-amino isobutyric acid (Aib).

The above amino acids, except M(OCH$_3$), are readily available materials. The synthesis of M(OCH$_3$) was conducted as shown in reaction (1) below which synthesis follows the procedures set forth in the art for the tritylation step, methylation and detritylation step[43,44]:

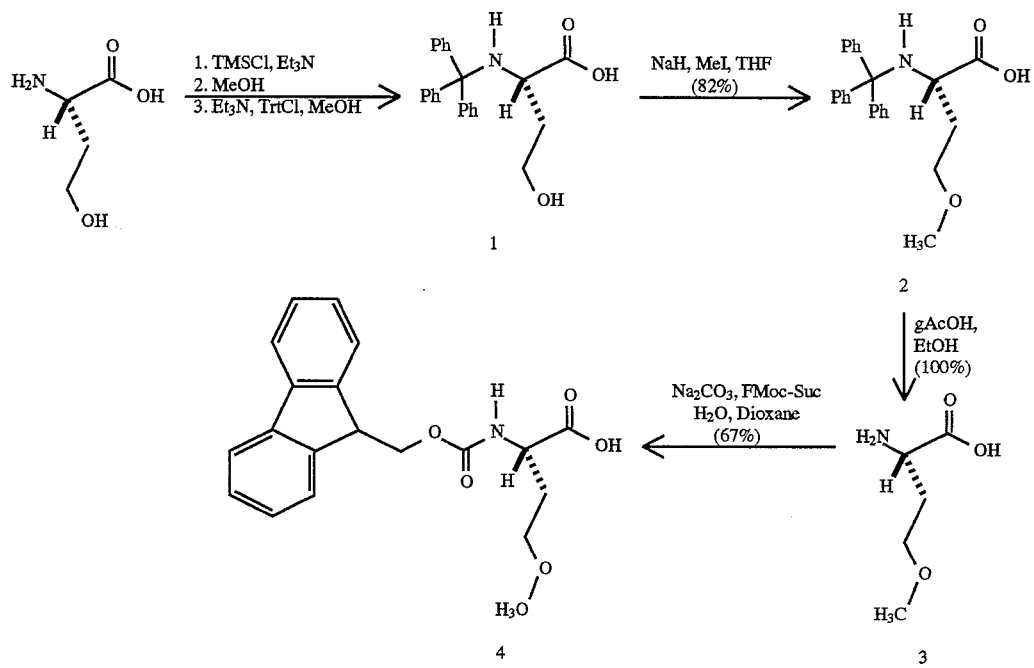

Specifically, to a stirred suspension of L-homoserine (8 grams, 67 mmol) in methylene chloride (120 mL) was added (CH₃)₃SiCl (30 mL, 234 mmol), and the mixture was refluxed for 30 minutes. It was then allowed to reach room temperature, treated with a solution of triethylamine (9.34 mL, mmol) in 120 mL of methylene chloride and refluxed for 45 minutes. The reaction mixture, at 0° C., was treated dropwise with anhydrous methanol (4 mL) in methylene chloride (250 mL) and allowed to attain room temperature. Then triethylamine (9.34 mL, 67 mmol) was added followed by the addition of trityl chloride (Trt-Cl) (18.8 grams, 67 mmol) over a 15 minute period. The reaction was stirred overnight. Evaporation under reduced pressure left a residue, which was partitioned between ethyl acetate (300 mL) and a 5% precooled aqueous solution of citric acid (200 mL). The organic layer was collected, washed with 1 N NaOH (150 mL) and water (150 mL). The combined aqueous layers were washed with ether (50 mL), cooled to 0° C., and neutralized with glacial acetic acid. The precipitated product was extracted with ethyl acetate (2×200 mL), and the combined organic layers were washed twice with saturated NaCl and dried (Na₂SO₃). Evaporation of the solvents in vacuo gave compound 1 (18 grams, 75% yield) as a white solid.

To a suspension of sodium hydride (11.9 grams, 80% in oil, 497 mmol) and imidazole (0.639 grams, 9.4 mmol) in tetrahydrofuran (350 mL), a solution of compound 1 (17.3 grams, 47 mmol) in tetrahydrofuran (120 mL) was added with stirring at −15° C. over 15 minutes. After 1 hour at that temperature, methyl iodide (6.23 mL, 100 mmol) was added and the mixture was stirred at −5° C. for 10 hours. The resulting mixture was subsequently diluted, at 0° C. with water (300 mL) and extracted with ether (2×100 mL). The cooled aqueous layer was then neutralized with glacial acetic acid and extracted with ethyl acetate. Organic layers were combined, washed with 5% citric acid and brine, dried (Na₂SO₃), and concentrated in vacuo. The residue was triturated with hexane to give compound 2 (15 grams, 85% yield) as a white powder.

A solution of compound Z (15 grams, 40 mmol) in ethanol (700 mL) was treated with acetic acid (71 mL) for 40 hours. The solvents were evaporated and the residue was triturated with hexane to give compound 3 (5 g, 94% yield) as a white crystalline powder.

By following the procedures set forth herein, the methoxy group of M(OCH₃), as described above, can be replaced by a higher homolog thereof such as an alkoxy group of from 2 to 10 carbon atoms.

When compound 2 is employed in the peptide synthesis, it is conventionally converted to the F-moc amino protected derivative. Such conversion is typically achieved as follows:

A solution of NaHCO₃ (8.4 g, 100 mmol) in water (200 mL) was added to a suspension of compound 3 (5 grams, 37 mmol) in dioxane (200 mL) at 0° C. After 10 minutes of stirring, F-moc succinimide (14.8 grams, 44 mmol) was added slowly to the resulting solution and stirring was continued until completion of the reaction (24 hours). The cooled reaction mixture was diluted with water and extracted with ether (3×50 mL). The aqueous layer was acidified with acetic acid and extracted with ethyl acetate (3×150 mL). The organic layer was washed with brine, concentrated to give a yellowish precipitate that was triturated with ether to give compound 4 (6 g, 46% yield) as a white powder.

Each of the above synthetic amino acids as well as 2-amino isobutryic acid were N-protected and the carboxyl group activated by conventional methods and then incorporated into several peptide structures. The resulting peptides so prepared were derivatives of the peptide DITWDQLWDLMK (SEQ ID NO 3) and included the following:

DITWDQLWDLMK-NH₂ (SEQ ID NO 167)
DITNal(1)DQLWDLMK-NH₂ (SEQ ID NO 118)
DITWDQLNal (1) DLMK-NH₂ (SEQ ID NO 119)
DITNal(2)DQLWDLMK-NH₂ (SEQ ID NO 120)
DITWDQLNal (2) DLMK-NH₂ (SEQ ID NO 121)
DITChaDQLWDLMK-NH₂ (SEQ ID NO 122)
DITWDQLChaDLMK-NH₂ (SEQ ID NO 123)
DITWDQLWDLM(OCH₃)K-NH₂ (SEQ ID NO 124)
DITWDQLWDLM(SOCH₃)K-NH₂ (SEQ ID NO 125)

DiTWDQLWDLM(SO₂CH₃)K-NH₂ (SEQ ID NO 126)
DITWDQLW-Aib-LMK-NH₂ (SEQ ID NO 127)
DITWDQLW-Aib-LMK-OH (SEQ ID NO 128)
DITW-Aib-QLWKLMK-OH (SEQ ID NO 129)
DITW-Aib-QLWDLMK-NH₂ (SEQ ID NO 130)
DITW-Aib-QLW-Aib-LMK-NH₂ (SEQ ID NO 131)
DITW-Aib-QLWDLMK-OH (SEQ ID NO 132)
DITW-Aib-QLW-Aib-LMK-OH (SEQ ID NO 133)
AITWDQLWDLNleK-OH (SEQ ID NO 134)
DATWDQLWDLNleK-OH (SEQ ID NO 135)
DITADQLWDLNleK-OH (SEQ ID NO 136)
DITWAQLWDLNleK-OH (SEQ ID NO 137)
DITWDALWDLNleK-OH (SEQ ID NO 138)
DITWDQAWDLNleK-OH (SEQ ID NO 139)
DITWDQLADLNleK-OH (SEQ ID NO 140)
DITWDQLWALNleK-OH (SEQ ID NO 141)
DITWDQLWDANleK-OH (SEQ ID NO 142)
DITWDQLWDLAK-OH (SEQ ID NO 143)
DITWDQLWDLNleA-OH (SEQ ID NO 144)
DITNal(1)DQLNal(1)DLMK-NH₂ (SEQ ID NO 145)
DITWAQLNal(1)DLMK-NH₂ (SEQ ID NO 146)
DITNal(1)AQLNal(1)DLMK-NH₂ ( SEQ ID NO 147 )
DITNal(1)AQLNal(1)DLM (OCH₃)K-NH₂ (SEQ ID NO 148)
DiTWAQLWDLM(SO₂CH₃)K-NH₂ (SEQ ID NO 149)
DiTWAQLNal(1)DLM(SO₂CH₃)K-NH₂ (SEQ ID NO 150)
DiTNal(1)AQLWDLM(SO₂CH₃)K-NH₂ (SEQ ID NO 151)
DITWAQLWDLM(OCH₃)K-NH₂ (SEQ ID NO 152)
DITNal(1)AQLWDLMK-NH₂ (SEQ ID NO 153)
DiTNal(1)DQLWDLM(SO₂CH₃)K-NH₂ (SEQ ID NO 154)
DiTWDQLNal(1)DLM(SO₂CH₃)K-NH₂ (SEQ ID NO 155)
DiTWAQLWDLMK-NH₂ (SEQ ID NO 156)
DITWAibQLWDLMK-NH₂ (SEQ ID NO 157)

Each of these peptides were assayed to determine their IC₅₀-standard in the manner described above in Example 2. The results of this assay indicated that each of the above peptides had an IC₅₀-standard of less than 1 mM indicating that peptides having one or more synthetic amino acids can nevertheless bind to E-selectin.

EXAMPLE 5

BINDING OF PEPTIDES MIMETICS TO E-SELECTIN

The following example demonstrates that peptide mimetics can also bind to E-selectin. Specifically, in this example, peptide mimetics having a C-terminal —C(O)NH₂ substituent were prepared by conventional solid phase synthetic methods. Other peptide mimetics prepared included N-terminal modifications such as acetylation (Ac), formation of a succinimide group at the N-terminus, or the formation of a CBZ group at the N-terminus via conventional methods described above. Examples of such peptide mimetics include the following:

Ac-DITWDQLWKLMK-OH (SEQ ID NO 168)
Ac-DITWDQLWDL-Nle-K-NH₂ (SEQ ID NO 158)
Succinimide-ITWDQLWDLMK-OH (SEQ ID NO 161)
Cbz-TWDQLWDLMK-OH (SEQ ID NO 163)
Succ-ITWDQLWDLMK-NH₂ (SEQ ID NO 159)
Cbz-DITWDQLWDLMK-NH₂ (SEQ ID NO 160)
Ac-DITWDQLWDLMK-NH₂ (SEQ ID NO 165)
(Ac=acetyl; Succ=succinimidyl)

Each of these peptide mimetics were assayed to determine their IC₅₀-standard in the manner described above in Example 2. The results of this assay indicated that each of the above peptide mimetics had an IC₅₀-standard of less than 1 mM indicating that peptide mimetics including those having more than one modification can nevertheless bind to E-selectin. The above results further indicate that the amino acid M(OCH₃) is a suitable replacement for methionine in the above peptides and, accordingly, is contemplated as a suitable for replacement in peptides containing methionine. In this embodiment, the present invention is directed to a method for creating a peptide mimetic which method comprises replacing at least one methionine amino acid groups in a peptide with M(OCH₃).

Although the foregoing invention has been described in some detail by way of illustration and example for purposes of clarity and understanding, it will be apparent that certain changes and modifications may be practiced within the scope of the appended claims.

What is claimed is:

1. A method for treating disease and disease symptoms which are mediated by the presence of ELAM-1 which method comprises the administration to a patient of an amount sufficient to reduce inflammation of a pharmaceutical composition comprising a peptide and/or peptide mimetic and a pharmaceutically acceptable carrier, wherein said peptide or peptide mimetic has a core sequence comprising WXXLWXXM (SEQ ID NO:1) where each amino acid is indicated by standard one letter abbreviations, and X is any amino acid.

2. The method of claim 1, wherein said peptide or peptide mimetic is 9 to 12 amino acid residues in length and comprises the sequence $X_1X_2X_3WX_4X_5LWX_6X_7X_8X_9$ (SEQ ID NO:2) wherein each residue can be independently selected as follows: $X_1$ is H, E, or D; $X_2$ is I, M, or Nle; $X_3$ is T or S; $X_4$ is D, E, or L; $X_5$ is Q or E; $X_6$ is N or D; $X_7$ is L, M, V, or I; $X_8$ is M or Nle; and $X_9$ is N, S or Q.

3. The method of claim 2, wherein said peptide is selected from the group consisting of a peptide comprising the sequence:

DITWDQLWDLMK (SEQ ID NO:3)
DGDITWDQLWDLMK (SEQ ID NO:4);
DITWDQLWDLNleK (SEQ ID NO:9);
d-DITWDQLWDLMK (SEQ ID NO:3);
Dd-ITWDQLWDLMK (SEQ ID NO:3);
ITWDQLWDLMK (amino acids 2–12 of SEQ ID NO:3);
DITNal(1)DQLWDLMK-NH$_2$ (SEQ ID NO:118);
DITWDQLNal(1)DLMK-NH$_2$ (SEQ ID NO:119);
DITNal(2)DQLWDLMK-NH$_2$ (SEQ ID NO:120);
DITWDQLNal(2)DLMK-NH$_2$ (SEQ ID NO:121);
DITChaDQLWDLMK-NH$_2$ (SEQ ID NO:122);
DITWDQLChaDLMK-NH$_2$ (SEQ ID NO:123);
DITWDQLWDLM(OCH$_3$)K-NH$_2$ (SEQ ID NO:124);
DITWDQLWDLM(SOCH$_3$)K-NH$_2$ (SEQ ID NO:125);
DITWDQLWDLM(SO$_2$CH$_3$)K-NH$_2$ (SEQ ID NO:126);
DITWDQLW-Aib-LMK-NH$_2$ (SEQ ID NO:127);
DITWDQLWDLMK-OH (SEQ ID NO:128);
DITW-Aib-QLWDLMK-NH$_2$ (SEQ ID NO:130);
DITW-Aib-QLWDLMK-OH (SEQ ID NO:132);
DITWDQLWDLAK-OH (SEQ ID NO:143);
DITWAQLWDLMK-NH$_2$ (SEQ ID NO:156);
Ac-DITWDQLWDLMK-OH (SEQ ID NO:3);
Succinimide-ITWDQLWDLMK-OH (amino acids 2–12 of SEQ ID NO:3);
Cbz-ITWDQLWDLMK-OH (amino acids 2–12 of SEQ ID NO:3);
Succ-ITWDQLWDLMK-NH$_2$ (SEQ ID NO:159); and
Ac-DITWDQLWDLMK-NH$_2$ (SEQ ID NO:160).

* * * * *

SEQUENCE LISTING ( 1 ) GENERAL INFORMATION:

( i i i ) NUMBER OF SEQUENCES: 169

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(2, 3, 6, 7)

( D ) OTHER INFORMATION: /note= "Xaa is any amino acid."

( x i ) SEQUENCE DESCRIPTION: SEQ ID NO:1:

Trp Xaa Xaa Leu Trp Xaa Xaa Met
1               5

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1)
        ( D ) OTHER INFORMATION: /note= "Xaa is His, Glu or Asp."

( i x ) FEATURE:
        ( A ) NAME/KEY: Region
        ( B ) LOCATION: one-of(2)
        ( D ) OTHER INFORMATION: /note= "Xaa is Ile, Met or
            Norleucine."

( i x ) FEATURE:
        ( A ) NAME/KEY: Region
        ( B ) LOCATION: one-of(3)
        ( D ) OTHER INFORMATION: /note= "Xaa is Thr or Ser."

( i x ) FEATURE:
        ( A ) NAME/KEY: Region
        ( B ) LOCATION: one-of(5)
        ( D ) OTHER INFORMATION: /note= "Xaa is Asp, Ala, Glu or
            Leu."

( i x ) FEATURE:
        ( A ) NAME/KEY: Region
        ( B ) LOCATION: one-of(10)
        ( D ) OTHER INFORMATION: /note= "Xaa is Leu, Met, Val or
            Ile."

( i x ) FEATURE:
        ( A ) NAME/KEY: Region
        ( B ) LOCATION: one-of(11)
        ( D ) OTHER INFORMATION: /note= "Xaa is Met, Norleucine,
            o-methyl methionine or met-sulfone."

( i x ) FEATURE:
        ( A ) NAME/KEY: Region
        ( B ) LOCATION: one-of(12)
        ( D ) OTHER INFORMATION: /note= "Xaa is Asn, Ser, Lys or
            Gln."

( x i ) SEQUENCE DESCRIPTION: SEQ ID NO:2:

Xaa Xaa Xaa Trp Xaa Glx Leu Trp Asx Xaa Xaa Xaa
1               5                   10

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Asp Ile Thr Trp Asp Gln Leu Trp Asp Leu Met Lys
1               5                   10

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Asp Gly Asp Ile Thr Trp Asp Gln Leu Trp Asp Leu Met Lys
 1           5                   10
```

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Asp Tyr Thr Trp Phe Glu Leu Trp Asp Met Met Gln
 1           5                   10
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Asp Ile Thr Trp Asp Glu Leu Trp Lys Ile Met Asn
 1           5                   10
```

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Gln Ile Thr Trp Ala Gln Leu Trp Asn Met Met Lys
 1           5                   10
```

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Asp Tyr Ser Trp His Asp Leu Trp Glu Met Met Ser
 1           5                   10
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(11)
        ( D ) OTHER INFORMATION: /note= "Xaa is Norleucine."

( x i ) SEQUENCE DESCRIPTION: SEQ ID NO:9:

Asp Ile Thr Trp Asp Gln Leu Trp Asp Leu Xaa Lys
1               5                   10

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

His Ile Thr Trp Asp Gln Leu Trp Arg Ile Met Thr
1               5                   10

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Tyr Asp Asp Val Cys Cys Glu Leu Leu Phe
1               5                   10

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Asp Leu Pro Gln Trp Tyr Thr Glu Trp Cys
1               5                   10

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Glu  Asn  Ser  His  Trp  Cys  Thr  Cys  Pro  Cys
1                   5                        10
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Asp  Ile  Glu  Gln  Asp  Trp  Val  Thr  Trp  Met
1                   5                        10
```

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Asn  Glu  Trp  Cys  Val  Val  Pro  Cys  Arg  Leu
1                   5                        10
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Asp  Ile  Trp  Gln  Asp  Trp  Val  Arg  Trp  Met
1                   5                        10
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Asp  Leu  Trp  Gln  Asp  Trp  Val  Thr  Trp  Met
1                   5                        10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Asp Leu Trp Gln Asp Trp Val His Trp Met
1               5                   10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Asp Ile Trp Gln Asp Trp Val Thr Trp Met
1               5                   10
```

( 2 ) INFORMATION FOR SEQ ID NO:20:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Asp Ile Trp Gln Asp Trp Val Lys Trp Met
1               5                   10
```

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Asp Ile Trp Glu Asp Trp Val Arg Trp Met
1               5                   10
```

( 2 ) INFORMATION FOR SEQ ID NO:22:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Asp Ile Trp Gln Asp Trp Ile Thr Trp Met
1               5                   10
```

( 2 ) INFORMATION FOR SEQ ID NO:23:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

His Ile Thr Trp Asp Gln Leu Trp Asn Val Met Asn
1               5                       10

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

His Ile Thr Trp Asp Gln Xaa Xaa Xaa Xaa Xaa Xaa
1               5                       10

( 2 ) INFORMATION FOR SEQ ID NO:25:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Xaa Xaa Thr Trp Asp Gln Leu Trp Xaa Xaa Xaa Xaa
1               5                       10

( 2 ) INFORMATION FOR SEQ ID NO:26:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Xaa Xaa Xaa Xaa Asp Gln Leu Trp Asn Val Xaa Xaa
1               5                       10

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

Xaa Xaa Xaa Xaa Xaa Xaa Leu Trp Asn Val Met Asn
1               5                       10

( 2 ) INFORMATION FOR SEQ ID NO:28:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
   Xaa Xaa Xaa Xaa His Ile Thr Trp Asp Gln Leu Trp Asn Val Met Asn
   1               5                   10                      15

Xaa Xaa Xaa Xaa
                20
```

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
   Xaa Xaa Xaa Trp Xaa Xaa Leu Trp Xaa Xaa Met Xaa
   1               5                   10
```

( 2 ) INFORMATION FOR SEQ ID NO:30:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

```
   Xaa Xaa Xaa Xaa Trp Xaa Xaa Leu Trp Xaa Xaa Met Xaa Xaa Xaa
   1               5                   10                  15

Xaa Xaa
```

( 2 ) INFORMATION FOR SEQ ID NO:31:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

```
   Ala Ile Thr Trp Asp Gln Leu Trp Leu Leu Met Ser
   1               5                   10
```

( 2 ) INFORMATION FOR SEQ ID NO:32:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

```
   Glu Leu Thr Trp Asp Gln Leu Trp Val Leu Met Ser
   1               5                   10
```

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:33:

```
Asp Val Thr Trp Asp Gln Leu Trp Glu Leu Met Thr
 1               5                   10
```

(2) INFORMATION FOR SEQ ID NO:34:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:34:

```
Glu Val Thr Trp Asp Gln Leu Trp Val Met Met Gln
 1               5                   10
```

(2) INFORMATION FOR SEQ ID NO:35:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:35:

```
Asn Leu Thr Trp Asp Gln Leu Trp Val Leu Met Ser
 1               5                   10
```

(2) INFORMATION FOR SEQ ID NO:36:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:36:

```
Glu Met Ser Trp Leu Glu Leu Trp Asn Val Met Asn
 1               5                   10
```

(2) INFORMATION FOR SEQ ID NO:37:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:37:

```
Thr Ile Thr Trp Asp Gln Leu Trp Gln Met Met Ser
 1               5                   10
```

(2) INFORMATION FOR SEQ ID NO:38:

(i) SEQUENCE CHARACTERISTICS:
    (A) LENGTH: 12 amino acids
    (B) TYPE: amino acid
    (C) STRANDEDNESS: single (D) TOPOLOGY: linear (ii) MOLECULE TYPE: peptide (xi) SEQUENCE DESCRIPTION: SEQ ID NO:38:

```
Glu Leu Ser Trp Asp Gln Leu Trp Asn Val Met Asn
1               5                   10
```

(2) INFORMATION FOR SEQ ID NO:39:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:39:

```
Glu Met Thr Trp Gln Glu Leu Trp Asn Val Met Asn
1               5                   10
```

(2) INFORMATION FOR SEQ ID NO:40:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:40:

```
Glu Met Thr Trp Thr Glu Leu Trp Asn Val Met Asn
1               5                   10
```

(2) INFORMATION FOR SEQ ID NO:41:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:41:

```
Asp Met Thr Trp Ser Gln Leu Trp Asn Val Met Asn
1               5                   10
```

(2) INFORMATION FOR SEQ ID NO:42:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:42:

```
Glu Met Thr Trp Leu Gly Leu Trp Asn Val Met Asn
1               5                   10
```

(2) INFORMATION FOR SEQ ID NO:43:

(i) SEQUENCE CHARACTERISTICS:
(A) LENGTH: 12 amino acids
(B) TYPE: amino acid
(C) STRANDEDNESS: single ( D ) TOPOLOGY: linear ( i i ) MOLECULE TYPE: peptide ( x i ) SEQUENCE DESCRIPTION: SEQ ID NO:43:

Gln  Ile  Thr  Trp  Met  Glu  Leu  Trp  Asn  Leu  Met  Asn
   1                   5                        10

( 2 ) INFORMATION FOR SEQ ID NO:44:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:44:

Glu  Ile  Thr  Trp  Asp  Gln  Leu  Trp  Glu  Val  Met  Asn
   1                   5                        10

( 2 ) INFORMATION FOR SEQ ID NO:45:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:45:

Glu  Ile  Thr  Trp  Asp  Gln  Leu  Trp  Asp  Val  Met  Asn
   1                   5                        10

( 2 ) INFORMATION FOR SEQ ID NO:46:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:46:

Asp  Ile  Ser  Trp  Asp  Gln  Leu  Trp  Asn  Val  Met  Asn
   1                   5                        10

( 2 ) INFORMATION FOR SEQ ID NO:47:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:47:

Gln  Ile  Thr  Trp  Asp  Gln  Leu  Trp  Asp  Leu  Met  Lys
   1                   5                        10

( 2 ) INFORMATION FOR SEQ ID NO:48:

( i ) SEQUENCE CHARACTERISTICS:
           ( A ) LENGTH: 12 amino acids
           ( B ) TYPE: amino acid
           ( C ) STRANDEDNESS: single (D) TOPOLOGY: linear (ii) MOLECULE TYPE: peptide (xi) SEQUENCE DESCRIPTION: SEQ ID NO:48:

```
Glu  Met  Thr  Trp  Asp  Gln  Leu  Trp  Asn  Val  Met  Asn
 1              5                        10
```

(2) INFORMATION FOR SEQ ID NO:49:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Asp  Ile  Thr  Trp  Asp  Gln  Leu  Trp  Asn  Met  Met  Asp
 1              5                        10
```

(2) INFORMATION FOR SEQ ID NO:50:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Asp  Ile  Thr  Trp  Asn  Met  Leu  Trp  Asn  Met  Met  Gln
 1              5                        10
```

(2) INFORMATION FOR SEQ ID NO:51:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

```
Asp  Ile  Ser  Trp  Asp  Asp  Leu  Trp  Ile  Met  Met  Asn
 1              5                        10
```

(2) INFORMATION FOR SEQ ID NO:52:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Asp  Ile  Thr  Trp  His  Gln  Leu  Trp  Asn  Leu  Met  Asn
 1              5                        10
```

(2) INFORMATION FOR SEQ ID NO:53:

(i) SEQUENCE CHARACTERISTICS:
        (A) LENGTH: 12 amino acids
        (B) TYPE: amino acid
        (C) STRANDEDNESS: single ( D ) TOPOLOGY: linear ( i i ) MOLECULE TYPE: peptide ( x i ) SEQUENCE DESCRIPTION: SEQ ID NO:53:

```
Glu Ile Ser Trp Glu Gln Leu Trp Thr Met Met Asn
1               5                   10
```

( 2 ) INFORMATION FOR SEQ ID NO:54:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:54:

```
Asp Ile Thr Trp Glu Gln Leu Trp Asn Met Met Asn
1               5                   10
```

( 2 ) INFORMATION FOR SEQ ID NO:55:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:55:

```
Glu Ile Thr Trp Asp Gln Leu Trp Thr Leu Met Thr
1               5                   10
```

( 2 ) INFORMATION FOR SEQ ID NO:56:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:56:

```
Asp Ile Thr Trp His Gln Leu Trp Asn Leu Met Asn
1               5                   10
```

( 2 ) INFORMATION FOR SEQ ID NO:57:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:57:

```
Asp Met Thr Trp Asp Gln Leu Trp Ile Val Met Asn
1               5                   10
```

( 2 ) INFORMATION FOR SEQ ID NO:58:

( i ) SEQUENCE CHARACTERISTICS:
      ( A ) LENGTH: 12 amino acids
      ( B ) TYPE: amino acid
      ( C ) STRANDEDNESS: single (D) TOPOLOGY: linear (ii) MOLECULE TYPE: peptide (xi) SEQUENCE DESCRIPTION: SEQ ID NO:58:

Asp Ile Thr Trp Glu Gln Leu Trp Asn Leu Met Asn
1               5                   10

(2) INFORMATION FOR SEQ ID NO:59:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:59:

Gln Ile Thr Trp Tyr Gln Leu Trp Asn Met Met Asn
1               5                   10

(2) INFORMATION FOR SEQ ID NO:60:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:60:

His Ile Ser Trp His Glu Leu Trp Asn Leu Met Gln
1               5                   10

(2) INFORMATION FOR SEQ ID NO:61:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:61:

Tyr Ile Thr Trp Glu Gln Leu Trp Thr Met Met Asn
1               5                   10

(2) INFORMATION FOR SEQ ID NO:62:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:62:

His Ile Thr Trp Asp Gln Leu Trp Asp Leu Met Gln
1               5                   10

(2) INFORMATION FOR SEQ ID NO:63:

(i) SEQUENCE CHARACTERISTICS:
    (A) LENGTH: 12 amino acids
    (B) TYPE: amino acid
    (C) STRANDEDNESS: single (D) TOPOLOGY: linear (ii) MOLECULE TYPE: peptide (xi) SEQUENCE DESCRIPTION: SEQ ID NO:63:

```
Gln Ile Thr Trp Asp Gln Leu Trp Asp Leu Met Tyr
1               5                   10
```

(2) INFORMATION FOR SEQ ID NO:64:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:64:

```
Gln Ile Thr Trp Asp Gln Leu Trp Asn Met Met Ile
1               5                   10
```

(2) INFORMATION FOR SEQ ID NO:65:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:65:

```
Tyr Ile Thr Trp Glu Gln Leu Trp Asn Met Met Asn
1               5                   10
```

(2) INFORMATION FOR SEQ ID NO:66:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:66:

```
His Ile Thr Trp Asp Gln Leu Trp Asp Ile Met Ser
1               5                   10
```

(2) INFORMATION FOR SEQ ID NO:67:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:67:

```
His Ile Thr Trp Asp Gln Leu Trp Glu Ile Met Ser
1               5                   10
```

(2) INFORMATION FOR SEQ ID NO:68:

(i) SEQUENCE CHARACTERISTICS:
(A) LENGTH: 12 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO:68:

His Ile Thr Trp Asp Gln Leu Trp Ala Leu Met Thr
1               5                   10

(2) INFORMATION FOR SEQ ID NO:69:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:69:

His Ile Thr Trp Asp Gln Leu Trp Ser Leu Met Ser
1               5                   10

(2) INFORMATION FOR SEQ ID NO:70:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:70:

His Ile Thr Trp Asp Gln Leu Trp Leu Met Met Ser
1               5                   10

(2) INFORMATION FOR SEQ ID NO:71:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:71:

His Ile Thr Trp Asp Gln Leu Trp Asp Leu Met Gln
1               5                   10

(2) INFORMATION FOR SEQ ID NO:72:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:72:

His Ile Thr Trp Asp Gln Leu Trp Trp Ile Met Ala
1               5                   10

(2) INFORMATION FOR SEQ ID NO:73:

(i) SEQUENCE CHARACTERISTICS:
    (A) LENGTH: 12 amino acids
    (B) TYPE: amino acid
    (C) STRANDEDNESS: single ( D ) TOPOLOGY: linear ( i i ) MOLECULE TYPE: peptide ( x i ) SEQUENCE DESCRIPTION: SEQ ID NO:73:

His Ile Thr Trp Asp Gln Leu Trp Leu Leu Met Ala
1               5                   10

( 2 ) INFORMATION FOR SEQ ID NO:74:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:74:

His Ile Thr Trp Asp Gln Leu Trp Met Leu Met Ala
1               5                   10

( 2 ) INFORMATION FOR SEQ ID NO:75:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:75:

Gly Ser Asp Ser His Ile Thr Trp Asp Glu Leu Trp Asn Leu Met Asn
1               5                   10                  15

Pro Val Leu Ala
            20

( 2 ) INFORMATION FOR SEQ ID NO:76:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:76:

Asn Trp Leu Asp Asp Ile Thr Trp Asp Glu Leu Trp Lys Ile Met Asn
1               5                   10                  15

Pro Ser Thr Ala
            20

( 2 ) INFORMATION FOR SEQ ID NO:77:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:77:

Glu Thr Asp Asp His Ile Thr Trp Asp Gln Leu Trp Arg Ile Met Thr
1               5                   10                  15

Ala Thr Met Ala

20

( 2 ) INFORMATION FOR SEQ ID NO:78:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:78:

```
Trp Thr Asp Thr His Ile Thr Trp Asp Gln Leu Trp His Phe Met Asn
1               5                   10                  15
Met Gly Glu Gln
            20
```

( 2 ) INFORMATION FOR SEQ ID NO:79:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

```
Gly Phe Gly Glu Ala Ile Thr Trp Asp Gln Leu Trp Asp Met Met Asn
1               5                   10                  15
Gly Glu Asp Ala
            20
```

( 2 ) INFORMATION FOR SEQ ID NO:80:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

```
Asn Val Ala Glu Gln Ile Thr Trp Asp Gln Leu Trp Asn Leu Met Ser
1               5                   10                  15
Val Gly Ser Ser
            20
```

( 2 ) INFORMATION FOR SEQ ID NO:81:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:81:

```
Gly Gln Thr Gly Leu Ile Thr Trp Asp Met Leu Trp Asn Leu Met Asn
1               5                   10                  15
Pro Val Gly Glu
            20
```

( 2 ) INFORMATION FOR SEQ ID NO:82:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:82:

Gly Thr Gly Asp His Ile Thr Trp Asp Gln Leu Trp Asn Leu Met Ile
1               5                   10                  15

Asn Glu Lys Gly
            20

( 2 ) INFORMATION FOR SEQ ID NO:83:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:83:

Glu Tyr Gly Arg His Ile Thr Trp Asp Gln Leu Trp Gln Leu Met Gln
1               5                   10                  15

Ser Ala Thr Ala
            20

( 2 ) INFORMATION FOR SEQ ID NO:84:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:84:

Met Asn Asn Trp His Val Ser Trp Glu Gln Leu Trp Asp Ile Met Asn
1               5                   10                  15

Gly Pro Pro Asn
            20

( 2 ) INFORMATION FOR SEQ ID NO:85:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:85:

Glu Ser Ala Ser His Ile Thr Trp Gly Gln Leu Trp Asp Leu Met Asn
1               5                   10                  15

Ala Ser Glu Val
            20

( 2 ) INFORMATION FOR SEQ ID NO:86:

( i ) SEQUENCE CHARACTERISTICS:
   ( A ) LENGTH: 20 amino acids
   ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:86:

Tyr Trp Arg Gly Asn Ile Thr Trp Asp Gln Leu Trp Asn Ile Met Asn
1               5                   10                  15

Ser Glu Tyr Ser
          20

(2) INFORMATION FOR SEQ ID NO:87:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:87:

Ala Gly Ala Ser His Ile Thr Trp Ala Gln Leu Trp Asn Met Met Asn
1               5                   10                  15

Gly Asn Glu Gly
          20

(2) INFORMATION FOR SEQ ID NO:88:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:88:

Glu Ser Trp Ala His Ile Thr Trp Asp Gln Leu Trp Asn Leu Met Asn
1               5                   10                  15

Met Gly Thr Gln
          20

(2) INFORMATION FOR SEQ ID NO:89:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:89:

Tyr Gly Asn Ser Asn Ile Thr Trp Asp Gln Leu Trp Ser Ile Met Asn
1               5                   10                  15

Arg Gln Thr Thr
          20

(2) INFORMATION FOR SEQ ID NO:90:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide ( x i ) SEQUENCE DESCRIPTION: SEQ ID NO:90:

Ala His Leu Pro His Ile Ser Trp Asp Thr Leu Trp His Ile Met Asn
1               5                       10                      15

Lys Gly Glu Lys
            20

( 2 ) INFORMATION FOR SEQ ID NO:91:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:91:

Glu Ser Ala Ser His Ile Thr Trp Gly Gln Leu Trp Asp Leu Met Asn
1               5                       10                      15

Ala Ser Glu Val
            20

( 2 ) INFORMATION FOR SEQ ID NO:92:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:92:

Met Asn Asn Trp His Val Ser Trp Glu Gln Leu Trp Asp Ile Met Asn
1               5                       10                      15

Gly Pro Pro Asn
            20

( 2 ) INFORMATION FOR SEQ ID NO:93:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:93:

Gly Phe Gly Glu Ala Ile Thr Trp Asp Gln Leu Trp Asp Met Met Asn
1               5                       10                      15

Gly Glu Asp Ala
            20

( 2 ) INFORMATION FOR SEQ ID NO:94:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:94:

Trp Thr Asp Thr His Ile Thr Trp Asp Gln Leu Trp His Phe Met Asn

Met Gly Glu Gln
20

(2) INFORMATION FOR SEQ ID NO:95:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:95:

Glu Met Thr Trp Ala Glu Leu Trp Thr Leu Met Glu
1               5                   10

(2) INFORMATION FOR SEQ ID NO:96:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:96:

Asp Ile Ser Trp Arg Gln Leu Trp Asp Ile Met Asn
1               5                   10

(2) INFORMATION FOR SEQ ID NO:97:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:97:

Glu Ile Ser Trp Leu Gly Leu Trp Asp Ile Met Asn
1               5                   10

(2) INFORMATION FOR SEQ ID NO:98:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:98:

Asp Met Thr Trp His Asp Leu Trp Thr Leu Met Ser
1               5                   10

(2) INFORMATION FOR SEQ ID NO:99:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:99:

Arg Gly Val Trp Gly Gly Leu Trp Ser Met Thr Trp
1               5                   10

( 2 ) INFORMATION FOR SEQ ID NO:100:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:100:

Glu Met Thr Trp Gln Gln Leu Trp Val Val Met Gln
1               5                   10

( 2 ) INFORMATION FOR SEQ ID NO:101:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:101:

Ala Glu Trp Thr Trp Asp Gln Leu Trp His Val Met Asn Pro Ala Glu
1               5                   10                  15

Ser Gln ( 2 ) INFORMATION FOR SEQ ID NO:102:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:102:

Arg Asn Met Ser Trp Leu Glu Leu Trp Glu His Met Lys
1               5                   10

( 2 ) INFORMATION FOR SEQ ID NO:103:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:103:

Ser Gln Val Thr Trp Asn Asp Leu Trp Ser Val Met Asn Pro Glu Val
1               5                   10                  15

Val Asn ( 2 ) INFORMATION FOR SEQ ID NO:104:

( i ) SEQUENCE CHARACTERISTICS:
      ( A ) LENGTH: 14 amino acids
      ( B ) TYPE: amino acid
      ( C ) STRANDEDNESS: single ( D ) TOPOLOGY: linear ( i i ) MOLECULE TYPE: peptide ( x i ) SEQUENCE DESCRIPTION: SEQ ID NO:104:

```
His  Arg  Ala  Glu  Trp  Leu  Ala  Leu  Trp  Glu  Gln  Met  Ser  Pro
1              5                        10
```

( 2 ) INFORMATION FOR SEQ ID NO:105:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:105:

```
Tyr  Lys  Lys  Glu  Trp  Leu  Glu  Leu  Trp  His  Gln  Met  Gln  Ala
1              5                        10
```

( 2 ) INFORMATION FOR SEQ ID NO:106:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:106:

```
Arg  Ser  Leu  Ser  Trp  Leu  Gln  Leu  Trp  Asp  Gln  Met  Lys
1              5                        10
```

( 2 ) INFORMATION FOR SEQ ID NO:107:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:107:

```
Lys  Glu  Gln  Gln  Trp  Arg  Asn  Leu  Trp  Lys  Met  Met  Ser
1              5                        10
```

( 2 ) INFORMATION FOR SEQ ID NO:108:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:108:

```
Lys  Lys  Glu  Asp  Trp  Leu  Ala  Leu  Trp  Arg  Ile  Met  Ser  Val  Pro  Asp
1              5                        10                        15
```

( 2 ) INFORMATION FOR SEQ ID NO:109:

( i ) SEQUENCE CHARACTERISTICS:
        ( A ) LENGTH: 13 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:109:

Arg Asn Met Ser Trp Leu Glu Leu Trp Glu His Met Lys
1               5                   10

( 2 ) INFORMATION FOR SEQ ID NO:110:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:110:

Gly Arg Pro Thr Trp Asn Glu Leu Trp Asp Met Met Gln Ala Pro
1               5                   10                  15

( 2 ) INFORMATION FOR SEQ ID NO:111:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:111:

Lys Arg Lys Gln Trp Ile Glu Leu Trp Asn Ile Met Ser
1               5                   10

( 2 ) INFORMATION FOR SEQ ID NO:112:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:112:

Lys Thr Ser Glu Trp Asn Asn Leu Trp Lys Leu Met Ser Gln
1               5                   10

( 2 ) INFORMATION FOR SEQ ID NO:113:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(13)
        ( D ) OTHER INFORMATION: /note= "Xaa is Norleucine."

( x i ) SEQUENCE DESCRIPTION: SEQ ID NO:113:

Asp Gly Asp Ile Thr Trp Asp Gln Leu Trp Asp Leu Xaa Lys
1               5                   10

( 2 ) INFORMATION FOR SEQ ID NO:114:

( i ) SEQUENCE CHARACTERISTICS:
  ( A ) LENGTH: 21 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:114:

```
Leu Arg Arg Ala Ser Leu Gly Asp Gly Asp Ile Thr Trp Asp Gln Leu
1               5                   10                  15
Trp Asp Leu Met Lys
            20
```

( 2 ) INFORMATION FOR SEQ ID NO:115:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: one-of(11)
  ( D ) OTHER INFORMATION: /note= "Xaa is Norleucine."

( x i ) SEQUENCE DESCRIPTION: SEQ ID NO:115:

```
Gln Ile Thr Trp Asp Gln Leu Trp Asp Leu Xaa Lys
1               5                   10
```

( 2 ) INFORMATION FOR SEQ ID NO:116:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:116:

```
Ala Glu Lys Trp Asp Gln Leu Trp His Val Met Asn Pro Ala Glu Ser
1               5                   10                  15
Gln
```

( 2 ) INFORMATION FOR SEQ ID NO:117:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: one-of(10,11)
  ( D ) OTHER INFORMATION: /note= "Xaa is Norleucine."

( x i ) SEQUENCE DESCRIPTION: SEQ ID NO:117:

```
Asp Ile Thr Trp Ala Gln Leu Trp Asn Xaa Xaa Asn
1               5                   10
```

( 2 ) INFORMATION FOR SEQ ID NO:118:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(4)
    ( D ) OTHER INFORMATION: /note= "Xaa is Nal(1)."

( i x ) FEATURE:
    ( A ) NAME/KEY: Region
    ( B ) LOCATION: one-of(12)
    ( D ) OTHER INFORMATION: /note= "C-terminal Lys is amidated."

( x i ) SEQUENCE DESCRIPTION: SEQ ID NO:118:

Asp Ile Thr Xaa Asp Gln Leu Trp Asp Leu Met Lys
1               5                   10

( 2 ) INFORMATION FOR SEQ ID NO:119:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(8)
    ( D ) OTHER INFORMATION: /note= "Xaa is Nal(1)."

( i x ) FEATURE:
    ( A ) NAME/KEY: Region
    ( B ) LOCATION: one-of(12)
    ( D ) OTHER INFORMATION: /note= "C-terminal Lys is amidated."

( x i ) SEQUENCE DESCRIPTION: SEQ ID NO:119:

Asp Ile Thr Trp Asp Gln Leu Xaa Asp Leu Met Lys
1               5                   10

( 2 ) INFORMATION FOR SEQ ID NO:120:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(4)
    ( D ) OTHER INFORMATION: /note= "Xaa is Nal(2)."

( i x ) FEATURE:
    ( A ) NAME/KEY: Region
    ( B ) LOCATION: one-of(12)
    ( D ) OTHER INFORMATION: /note= "C-terminal Lys is amidated."

( x i ) SEQUENCE DESCRIPTION: SEQ ID NO:120:

Asp Ile Thr Xaa Asp Gln Leu Trp Asp Leu Met Lys
1               5                   10

( 2 ) INFORMATION FOR SEQ ID NO:121:

( i ) SEQUENCE CHARACTERISTICS:
    ( A ) LENGTH: 12 amino acids ( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(8)
( D ) OTHER INFORMATION: /note= "Xaa is Nal(2)."

( i x ) FEATURE:
( A ) NAME/KEY: Region
( B ) LOCATION: one-of(12)
( D ) OTHER INFORMATION: /note= "C-terminal Lys is amidated."

( x i ) SEQUENCE DESCRIPTION: SEQ ID NO:121:

Asp Ile Thr Trp Asp Gln Leu Xaa Asp Leu Met Lys
1               5                   10

( 2 ) INFORMATION FOR SEQ ID NO:122:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(4)
( D ) OTHER INFORMATION: /note= "Xaa is Cha."

( i x ) FEATURE:
( A ) NAME/KEY: Region
( B ) LOCATION: one-of(12)
( D ) OTHER INFORMATION: /note= "C-terminal Lys is amidated."

( x i ) SEQUENCE DESCRIPTION: SEQ ID NO:122:

Asp Ile Thr Xaa Asp Gln Leu Trp Asp Leu Met Lys
1               5                   10

( 2 ) INFORMATION FOR SEQ ID NO:123:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(8)
( D ) OTHER INFORMATION: /note= "Xaa is Cha."

( i x ) FEATURE:
( A ) NAME/KEY: Region
( B ) LOCATION: one-of(12)
( D ) OTHER INFORMATION: /note= "C-terminal Lys is amidated."

( x i ) SEQUENCE DESCRIPTION: SEQ ID NO:123:

Asp Ile Thr Trp Asp Gln Leu Xaa Asp Leu Met Lys
1               5                   10

( 2 ) INFORMATION FOR SEQ ID NO:124:

( i ) SEQUENCE CHARACTERISTICS:
( A ) LENGTH: 12 amino acids
( B ) TYPE: amino acid
( C ) STRANDEDNESS: single ( D ) TOPOLOGY: linear ( i i ) MOLECULE TYPE: peptide ( i x ) FEATURE:
    ( A ) NAME/KEY: Region
    ( B ) LOCATION: one-of(11)
    ( D ) OTHER INFORMATION: /note= "Xaa is M(OCH-3)."

( i x ) FEATURE:
    ( A ) NAME/KEY: Region
    ( B ) LOCATION: one-of(12)
    ( D ) OTHER INFORMATION: /note= "C-terminal Lys is amidated."

( x i ) SEQUENCE DESCRIPTION: SEQ ID NO:124:

Asp Ile Thr Trp Asp Gln Leu Trp Asp Leu Xaa Lys
1               5                   10

( 2 ) INFORMATION FOR SEQ ID NO:125:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(11)
        ( D ) OTHER INFORMATION: /note= "Xaa is M(SOCH-3)."

( i x ) FEATURE:
        ( A ) NAME/KEY: Region
        ( B ) LOCATION: one-of(12)
        ( D ) OTHER INFORMATION: /note= "C-terminal Lys is amidated."

( x i ) SEQUENCE DESCRIPTION: SEQ ID NO:125:

Asp Ile Thr Trp Asp Gln Leu Trp Asp Leu Xaa Lys
1               5                   10

( 2 ) INFORMATION FOR SEQ ID NO:126:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(11)
        ( D ) OTHER INFORMATION: /note= "Xaa is M(SO-2CH-3)."

( i x ) FEATURE:
        ( A ) NAME/KEY: Region
        ( B ) LOCATION: one-of(12)
        ( D ) OTHER INFORMATION: /note= "C-terminal Lys is amidated."

( x i ) SEQUENCE DESCRIPTION: SEQ ID NO:126:

Asp Ile Thr Trp Asp Gln Leu Trp Asp Leu Xaa Lys
1               5                   10

( 2 ) INFORMATION FOR SEQ ID NO:127:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Region
    ( B ) LOCATION: one-of(9)
    ( D ) OTHER INFORMATION: /note= "Xaa is 2-amino isobutyric
        acid."

( i x ) FEATURE:
    ( A ) NAME/KEY: Region
    ( B ) LOCATION: one-of(12)
    ( D ) OTHER INFORMATION: /note= "C-terminal Lys is amidated."

( x i ) SEQUENCE DESCRIPTION: SEQ ID NO:127:

```
Asp Ile Thr Trp Asp Gln Leu Trp Xaa Leu Met Lys
1               5                   10
```

( 2 ) INFORMATION FOR SEQ ID NO:128:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(9)
    ( D ) OTHER INFORMATION: /note= "Xaa is 2-amino isobutyric
        acid."

( i x ) FEATURE:
    ( A ) NAME/KEY: Region
    ( B ) LOCATION: one-of(12)
    ( D ) OTHER INFORMATION: /note= "C-terminal Lys is
        hydroxylated."

( x i ) SEQUENCE DESCRIPTION: SEQ ID NO:128:

```
Asp Ile Thr Trp Asp Gln Leu Trp Xaa Leu Met Lys
1               5                   10
```

( 2 ) INFORMATION FOR SEQ ID NO:129:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(5)
    ( D ) OTHER INFORMATION: /note= "Xaa is 2-amino isobutyric
        acid."

( i x ) FEATURE:
    ( A ) NAME/KEY: Region
    ( B ) LOCATION: one-of(12)
    ( D ) OTHER INFORMATION: /note= "C-terminal Lys is
        hydroxylated."

( x i ) SEQUENCE DESCRIPTION: SEQ ID NO:129:

```
Asp Ile Thr Trp Xaa Gln Leu Trp Lys Leu Met Lys
1               5                   10
```

( 2 ) INFORMATION FOR SEQ ID NO:130:

( i ) SEQUENCE CHARACTERISTICS:
    ( A ) LENGTH: 12 amino acids
    ( B ) TYPE: amino acid ( C ) STRANDEDNESS: single
                    ( D ) TOPOLOGY: linear ( i i ) MOLECULE TYPE: peptide ( i x ) FEATURE:
                    ( A ) NAME/KEY: Region
                    ( B ) LOCATION: one-of(5)
                    ( D ) OTHER INFORMATION: /note= "Xaa is 2-amino isobutyric
                            acid."

( i x ) FEATURE:
                    ( A ) NAME/KEY: Region
                    ( B ) LOCATION: one-of(12)
                    ( D ) OTHER INFORMATION: /note= "C-terminal Lys is amidated."

( x i ) SEQUENCE DESCRIPTION: SEQ ID NO:130:

Asp  Ile  Thr  Trp  Xaa  Gln  Leu  Trp  Asp  Leu  Met  Lys
1                   5                        10

( 2 ) INFORMATION FOR SEQ ID NO:131:

( i ) SEQUENCE CHARACTERISTICS:
                    ( A ) LENGTH: 12 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Region
                    ( B ) LOCATION: one-of(5)
                    ( D ) OTHER INFORMATION: /note= "Xaa is 2-amino isobutyric
                            acid."

( i x ) FEATURE:
                    ( A ) NAME/KEY: Region
                    ( B ) LOCATION: one-of(9)
                    ( D ) OTHER INFORMATION: /note= "Xaa is 2-amino isobutyric
                            acid."

( i x ) FEATURE:
                    ( A ) NAME/KEY: Region
                    ( B ) LOCATION: one-of(12)
                    ( D ) OTHER INFORMATION: /note= "C-terminal Lys is amidated."

( x i ) SEQUENCE DESCRIPTION: SEQ ID NO:131:

Asp  Ile  Thr  Trp  Xaa  Gln  Leu  Trp  Xaa  Leu  Met  Lys
1                   5                        10

( 2 ) INFORMATION FOR SEQ ID NO:132:

( i ) SEQUENCE CHARACTERISTICS:
                    ( A ) LENGTH: 12 amino acids
                    ( B ) TYPE: amino acid
                    ( C ) STRANDEDNESS: single
                    ( D ) TOPOLOGY: linear ( i i ) MOLECULE TYPE: peptide ( i x ) FEATURE:
                    ( A ) NAME/KEY: Region
                    ( B ) LOCATION: one-of(5)
                    ( D ) OTHER INFORMATION: /note= "Xaa is 2-amino isobutyric
                            acid."

( i x ) FEATURE:
                    ( A ) NAME/KEY: Region
                    ( B ) LOCATION: one-of(12)
                    ( D ) OTHER INFORMATION: /note= "C-terminal Lys is
                            hydroxylated."

( x i ) SEQUENCE DESCRIPTION: SEQ ID NO:132:

Asp  Ile  Thr  Trp  Xaa  Gln  Leu  Trp  Asp  Leu  Met  Lys (2) INFORMATION FOR SEQ ID NO:133:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(5)
        (D) OTHER INFORMATION: /note= "Xaa is 2-amino isobutyric acid."

(ix) FEATURE:
        (A) NAME/KEY: Region
        (B) LOCATION: one-of(9)
        (D) OTHER INFORMATION: /note= "Xaa is 2-amino isobutyric acid."

(ix) FEATURE:
        (A) NAME/KEY: Region
        (B) LOCATION: one-of(12)
        (D) OTHER INFORMATION: /note= "C-terminal Lys is hydroxylated."

(xi) SEQUENCE DESCRIPTION: SEQ ID NO:133:

```
Asp Ile Thr Trp Xaa Gln Leu Trp Xaa Leu Met Lys
 1               5                   10
```

(2) INFORMATION FOR SEQ ID NO:134:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is Norleucine."

(ix) FEATURE:
        (A) NAME/KEY: Region
        (B) LOCATION: one-of(12)
        (D) OTHER INFORMATION: /note= "C-terminal Lys is hydroxylated."

(xi) SEQUENCE DESCRIPTION: SEQ ID NO:134:

```
Ala Ile Thr Trp Asp Gln Leu Trp Asp Leu Xaa Lys
 1               5                   10
```

(2) INFORMATION FOR SEQ ID NO:135:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is Norleucine."

(ix) FEATURE:

(A) NAME/KEY: Region
(B) LOCATION: one-of(12)
(D) OTHER INFORMATION: /note= "C-terminal Lys is hydroxylated."

(xi) SEQUENCE DESCRIPTION: SEQ ID NO:135:

```
Asp Ala Thr Trp Asp Gln Leu Trp Asp Leu Xaa Lys
1               5                   10
```

(2) INFORMATION FOR SEQ ID NO:136:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(11)
(D) OTHER INFORMATION: /note= "Xaa is Norleucine."

(ix) FEATURE:
(A) NAME/KEY: Region
(B) LOCATION: one-of(12)
(D) OTHER INFORMATION: /note= "C-terminal Lys is hydroxylated."

(xi) SEQUENCE DESCRIPTION: SEQ ID NO:136:

```
Asp Ile Thr Ala Asp Gln Leu Trp Asp Leu Xaa Lys
1               5                   10
```

(2) INFORMATION FOR SEQ ID NO:137:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(11)
(D) OTHER INFORMATION: /note= "Xaa is Norleucine."

(ix) FEATURE:
(A) NAME/KEY: Region
(B) LOCATION: one-of(12)
(D) OTHER INFORMATION: /note= "C-terminal Lys is hydroxylated."

(xi) SEQUENCE DESCRIPTION: SEQ ID NO:137:

```
Asp Ile Thr Trp Ala Gln Leu Trp Asp Leu Xaa Lys
1               5                   10
```

(2) INFORMATION FOR SEQ ID NO:138:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: one-of(11)
(D) OTHER INFORMATION: /note= "Xaa is Norleucine."

( i x ) FEATURE:
    ( A ) NAME/KEY: Region
    ( B ) LOCATION: one-of(12)
    ( D ) OTHER INFORMATION: /note= "C-terminal Lys is
        hydroxylated."

( x i ) SEQUENCE DESCRIPTION: SEQ ID NO:138:

Asp Ile Thr Trp Asp Ala Leu Trp Asp Leu Xaa Lys
1               5                   10

( 2 ) INFORMATION FOR SEQ ID NO:139:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(11)
    ( D ) OTHER INFORMATION: /note= "Xaa is Norleucine."

( i x ) FEATURE:
    ( A ) NAME/KEY: Region
    ( B ) LOCATION: one-of(12)
    ( D ) OTHER INFORMATION: /note= "C-terminal Lys is
        hydroxylated."

( x i ) SEQUENCE DESCRIPTION: SEQ ID NO:139:

Asp Ile Thr Trp Asp Gln Ala Trp Asp Leu Xaa Lys
1               5                   10

( 2 ) INFORMATION FOR SEQ ID NO:140:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(11)
    ( D ) OTHER INFORMATION: /note= "Xaa is Norleucine."

( i x ) FEATURE:
    ( A ) NAME/KEY: Region
    ( B ) LOCATION: one-of(12)
    ( D ) OTHER INFORMATION: /note= "C-terminal Lys is
        hydroxylated."

( x i ) SEQUENCE DESCRIPTION: SEQ ID NO:140:

Asp Ile Thr Trp Asp Gln Leu Ala Asp Leu Xaa Lys
1               5                   10

( 2 ) INFORMATION FOR SEQ ID NO:141:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(11)
    ( D ) OTHER INFORMATION: /note= "Xaa is Norleucine."

( i x ) FEATURE:
    ( A ) NAME/KEY: Region
    ( B ) LOCATION: one-of(12)
    ( D ) OTHER INFORMATION: /note= "C-terminal Lys is
        hydroxylated."

( x i ) SEQUENCE DESCRIPTION: SEQ ID NO:141:

Asp Ile Thr Trp Asp Gln Leu Trp Ala Leu Xaa Lys
1               5                   10

( 2 ) INFORMATION FOR SEQ ID NO:142:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(11)
        ( D ) OTHER INFORMATION: /note= "Xaa is Norleucine."

( i x ) FEATURE:
        ( A ) NAME/KEY: Region
        ( B ) LOCATION: one-of(12)
        ( D ) OTHER INFORMATION: /note= "C-terminal Lys is
            hydroxylated."

( x i ) SEQUENCE DESCRIPTION: SEQ ID NO:142:

Asp Ile Thr Trp Asp Gln Leu Trp Asp Ala Xaa Lys
1               5                   10

( 2 ) INFORMATION FOR SEQ ID NO:143:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(12)
        ( D ) OTHER INFORMATION: /note= "C-terminal Lys is
            hydroxylated."

( x i ) SEQUENCE DESCRIPTION: SEQ ID NO:143:

Asp Ile Thr Trp Asp Gln Leu Trp Asp Leu Ala Lys
1               5                   10

( 2 ) INFORMATION FOR SEQ ID NO:144:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(11)
        ( D ) OTHER INFORMATION: /note= "Xaa is Norleucine."

( i x ) FEATURE:
        ( A ) NAME/KEY: Region
        ( B ) LOCATION: one-of(12)

(D) OTHER INFORMATION: /note= "C-terminal Ala is hydroxylated."

(xi) SEQUENCE DESCRIPTION: SEQ ID NO:144:

Asp Ile Thr Trp Asp Gln Leu Trp Asp Leu Xaa Ala
1               5                   10

(2) INFORMATION FOR SEQ ID NO:145:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Region
      (B) LOCATION: one-of(4)
      (D) OTHER INFORMATION: /note= "Xaa is Nal(1)."

(ix) FEATURE:
      (A) NAME/KEY: Region
      (B) LOCATION: one-of(8)
      (D) OTHER INFORMATION: /note= "Xaa is Nal(1)."

(ix) FEATURE:
      (A) NAME/KEY: Region
      (B) LOCATION: one-of(12)
      (D) OTHER INFORMATION: /note= "C-terminal Lys is amidated."

(xi) SEQUENCE DESCRIPTION: SEQ ID NO:145:

Asp Ile Thr Xaa Asp Gln Leu Xaa Asp Leu Met Lys
1               5                   10

(2) INFORMATION FOR SEQ ID NO:146:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Region
      (B) LOCATION: one-of(8)
      (D) OTHER INFORMATION: /note= "Xaa is Nal(1)."

(ix) FEATURE:
      (A) NAME/KEY: Region
      (B) LOCATION: one-of(12)
      (D) OTHER INFORMATION: /note= "C-terminal Lys is amidated."

(xi) SEQUENCE DESCRIPTION: SEQ ID NO:146:

Asp Ile Thr Trp Ala Gln Leu Xaa Asp Leu Met Lys
1               5                   10

(2) INFORMATION FOR SEQ ID NO:147:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Region
      (B) LOCATION: one-of(4)
      (D) OTHER INFORMATION: /note= "Xaa is Nal(1)."

( i x ) FEATURE:
  ( A ) NAME/KEY: Region
  ( B ) LOCATION: one-of(8)
  ( D ) OTHER INFORMATION: /note= "Xaa is Nal(1)."

( i x ) FEATURE:
  ( A ) NAME/KEY: Region
  ( B ) LOCATION: one-of(12)
  ( D ) OTHER INFORMATION: /note= "C-terminal Lys is amidated."

( x i ) SEQUENCE DESCRIPTION: SEQ ID NO:147:

Asp Ile Thr Xaa Ala Gln Leu Xaa Asp Leu Met Lys
1               5                   10

( 2 ) INFORMATION FOR SEQ ID NO:148:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: one-of(4)
  ( D ) OTHER INFORMATION: /note= "Xaa is Nal(1)."

( i x ) FEATURE:
  ( A ) NAME/KEY: Region
  ( B ) LOCATION: one-of(8)
  ( D ) OTHER INFORMATION: /note= "Xaa is Nal(1)."

( i x ) FEATURE:
  ( A ) NAME/KEY: Region
  ( B ) LOCATION: one-of(11)
  ( D ) OTHER INFORMATION: /note= "Xaa is M(OCH-3)."

( i x ) FEATURE:
  ( A ) NAME/KEY: Region
  ( B ) LOCATION: one-of(12)
  ( D ) OTHER INFORMATION: /note= "C-terminal Lys is amidated."

( x i ) SEQUENCE DESCRIPTION: SEQ ID NO:148:

Asp Ile Thr Xaa Ala Gln Leu Xaa Asp Leu Xaa Lys
1               5                   10

( 2 ) INFORMATION FOR SEQ ID NO:149:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: one-of(11)
  ( D ) OTHER INFORMATION: /note= "Xaa is M(SO-2CH-3)."

( i x ) FEATURE:
  ( A ) NAME/KEY: Region
  ( B ) LOCATION: one-of(12)
  ( D ) OTHER INFORMATION: /note= "C-terminal Lys is amidated."

( x i ) SEQUENCE DESCRIPTION: SEQ ID NO:149:

Asp Ile Thr Trp Ala Gln Leu Trp Asp Leu Xaa Lys
1               5                   10

( 2 ) INFORMATION FOR SEQ ID NO:150:

( i ) SEQUENCE CHARACTERISTICS:
 ( A ) LENGTH: 12 amino acids
 ( B ) TYPE: amino acid
 ( C ) STRANDEDNESS: single
 ( D ) TOPOLOGY: linear ( i i ) MOLECULE TYPE: peptide ( i x ) FEATURE:
 ( A ) NAME/KEY: Region
 ( B ) LOCATION: one-of(8)
 ( D ) OTHER INFORMATION: /note= "Xaa is Nal(1)."

( i x ) FEATURE:
 ( A ) NAME/KEY: Region
 ( B ) LOCATION: one-of(11)
 ( D ) OTHER INFORMATION: /note= "Xaa is M(SO-2CH-3)."

( i x ) FEATURE:
 ( A ) NAME/KEY: Region
 ( B ) LOCATION: one-of(12)
 ( D ) OTHER INFORMATION: /note= "C-terminal Lys is amidated."

( x i ) SEQUENCE DESCRIPTION: SEQ ID NO:150:

```
Asp Ile Thr Trp Ala Gln Leu Xaa Asp Leu Xaa Lys
1               5                   10
```

( 2 ) INFORMATION FOR SEQ ID NO:151:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: one-of(4)
  ( D ) OTHER INFORMATION: /note= "Xaa is Nal(1)."

( i x ) FEATURE:
  ( A ) NAME/KEY: Region
  ( B ) LOCATION: one-of(11)
  ( D ) OTHER INFORMATION: /note= "Xaa is M(SO-2CH-3)."

( i x ) FEATURE:
  ( A ) NAME/KEY: Region
  ( B ) LOCATION: one-of(12)
  ( D ) OTHER INFORMATION: /note= "C-terminal Lys is amidated."

( x i ) SEQUENCE DESCRIPTION: SEQ ID NO:151:

```
Asp Ile Thr Xaa Ala Gln Leu Trp Asp Leu Xaa Lys
1               5                   10
```

( 2 ) INFORMATION FOR SEQ ID NO:152:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: one-of(11)
  ( D ) OTHER INFORMATION: /note= "Xaa is M(OCH-3)."

( i x ) FEATURE:
  ( A ) NAME/KEY: Region
  ( B ) LOCATION: one-of(12)
  ( D ) OTHER INFORMATION: /note= "C-terminal Lys is amidated."

( x i ) SEQUENCE DESCRIPTION: SEQ ID NO:152:

Asp Ile Thr Trp Ala Gln Leu Trp Asp Leu Xaa Lys
1               5                   10

( 2 ) INFORMATION FOR SEQ ID NO:153:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(4)
        ( D ) OTHER INFORMATION: /note= "Xaa is Nal(1)."

( i x ) FEATURE:
        ( A ) NAME/KEY: Region
        ( B ) LOCATION: one-of(12)
        ( D ) OTHER INFORMATION: /note= "C-terminal Lys is amidated."

( x i ) SEQUENCE DESCRIPTION: SEQ ID NO:153:

Asp Ile Thr Xaa Ala Gln Leu Trp Asp Leu Met Lys
1               5                   10

( 2 ) INFORMATION FOR SEQ ID NO:154:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(4)
        ( D ) OTHER INFORMATION: /note= "Xaa is Nal(1)."

( i x ) FEATURE:
        ( A ) NAME/KEY: Region
        ( B ) LOCATION: one-of(11)
        ( D ) OTHER INFORMATION: /note= "Xaa is M(SO-2CH-3)."

( i x ) FEATURE:
        ( A ) NAME/KEY: Region
        ( B ) LOCATION: one-of(12)
        ( D ) OTHER INFORMATION: /note= "C-terminal Lys is amidated."

( x i ) SEQUENCE DESCRIPTION: SEQ ID NO:154:

Asp Ile Thr Xaa Asp Gln Leu Trp Asp Leu Xaa Lys
1               5                   10

( 2 ) INFORMATION FOR SEQ ID NO:155:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(8)
        ( D ) OTHER INFORMATION: /note= "Xaa is Nal(1)."

( i x ) FEATURE:

( A ) NAME/KEY: Region
( B ) LOCATION: one-of(11)
( D ) OTHER INFORMATION: /note= "Xaa is M(SO-2CH-3)."

( i x ) FEATURE:
( A ) NAME/KEY: Region
( B ) LOCATION: one-of(12)
( D ) OTHER INFORMATION: /note= "C-terminal Lys is amidated."

( x i ) SEQUENCE DESCRIPTION: SEQ ID NO:155:

```
Asp Ile Thr Trp Asp Gln Leu Xaa Asp Leu Xaa Lys
1               5                   10
```

( 2 ) INFORMATION FOR SEQ ID NO:156:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(12)
( D ) OTHER INFORMATION: /note= "C-terminal Lys is amidated."

( x i ) SEQUENCE DESCRIPTION: SEQ ID NO:156:

```
Asp Ile Thr Trp Ala Gln Leu Trp Asp Leu Met Lys
1               5                   10
```

( 2 ) INFORMATION FOR SEQ ID NO:157:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(5)
( D ) OTHER INFORMATION: /note= "Xaa is 2-amino isobutyric
     acid."

( i x ) FEATURE:
( A ) NAME/KEY: Region
( B ) LOCATION: one-of(12)
( D ) OTHER INFORMATION: /note= "C-terminal Lys is amidated."

( x i ) SEQUENCE DESCRIPTION: SEQ ID NO:157:

```
Asp Ile Thr Trp Xaa Gln Leu Trp Asp Leu Met Lys
1               5                   10
```

( 2 ) INFORMATION FOR SEQ ID NO:158:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Region
( B ) LOCATION: one-of(1)
( D ) OTHER INFORMATION: /note= "N-terminal Asp is acetylated."

( i x ) FEATURE:
( A ) NAME/KEY: Region ( B ) LOCATION: one-of(11)
( D ) OTHER INFORMATION: /note= "Xaa is Norleucine."

( i x ) FEATURE:
    ( A ) NAME/KEY: Region
    ( B ) LOCATION: one-of(12)
    ( D ) OTHER INFORMATION: /note= "C-terminal Lys is amidated."

( x i ) SEQUENCE DESCRIPTION: SEQ ID NO:158:

```
Asp Ile Thr Trp Asp Gln Leu Trp Asp Leu Xaa Lys
1               5                   10
```

( 2 ) INFORMATION FOR SEQ ID NO:159:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1)
        ( D ) OTHER INFORMATION: /note= "N-terminal Ile is
            succinimidylated."

( i x ) FEATURE:
        ( A ) NAME/KEY: Region
        ( B ) LOCATION: one-of(11)
        ( D ) OTHER INFORMATION: /note= "C-terminal Lys is amidated."

( x i ) SEQUENCE DESCRIPTION: SEQ ID NO:159:

```
Ile Thr Trp Asp Gln Leu Trp Asp Leu Met Lys
1               5                   10
```

( 2 ) INFORMATION FOR SEQ ID NO:160:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:160:

```
Ile Thr Trp Asp Gln Leu Trp Asp Leu Met Lys
1               5                   10
```

( 2 ) INFORMATION FOR SEQ ID NO:161:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1)
        ( D ) OTHER INFORMATION: /note= "N-terminal Ile is modified with
            succinimide."

( i x ) FEATURE:
        ( A ) NAME/KEY: Region
        ( B ) LOCATION: one-of(11)
        ( D ) OTHER INFORMATION: /note= "C-terminal Lys is
            hydroxylated."

( x i ) SEQUENCE DESCRIPTION: SEQ ID NO:161:

```
    Ile  Thr  Trp  Asp  Gln  Leu  Trp  Asp  Leu  Met  Lys
    1                  5                       10
```

( 2 ) INFORMATION FOR SEQ ID NO:162:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:162:

```
    Thr  Trp  Asp  Gln  Leu  Trp  Asp  Leu  Met  Lys
    1                  5                       10
```

( 2 ) INFORMATION FOR SEQ ID NO:163:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(1)
        ( D ) OTHER INFORMATION: /note= "N-terminal Thr is modified with
            benxyloxycarbonyl."

( i x ) FEATURE:
        ( A ) NAME/KEY: Region
        ( B ) LOCATION: one-of(10)
        ( D ) OTHER INFORMATION: /note= "C-terminal Lys is
            hydroxylated."

( x i ) SEQUENCE DESCRIPTION: SEQ ID NO:163:

```
    Thr  Trp  Asp  Gln  Leu  Trp  Asp  Leu  Met  Lys
    1                  5                       10
```

( 2 ) INFORMATION FOR SEQ ID NO:164:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: one-of(10)
        ( D ) OTHER INFORMATION: /note= "C-terminal Met is amidated."

( x i ) SEQUENCE DESCRIPTION: SEQ ID NO:164:

```
    Asp  Ile  Trp  Gln  Asp  Trp  Val  Arg  Trp  Met
    1                  5                       10
```

( 2 ) INFORMATION FOR SEQ ID NO:165:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
  ( A ) NAME/KEY: Region
  ( B ) LOCATION: one-of(1)
  ( D ) OTHER INFORMATION: /note= "N-terminal Asp is acetylated."

( i x ) FEATURE:
  ( A ) NAME/KEY: Region
  ( B ) LOCATION: one-of(12)
  ( D ) OTHER INFORMATION: /note= "C-terminal Lys is amidated."

( x i ) SEQUENCE DESCRIPTION: SEQ ID NO:165:

Asp Ile Thr Trp Asp Gln Leu Trp Asp Leu Met Lys
1               5                   10

( 2 ) INFORMATION FOR SEQ ID NO:166:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(12)
    ( D ) OTHER INFORMATION: /note= "C-terminal Lys is modified with CONH-2."

( x i ) SEQUENCE DESCRIPTION: SEQ ID NO:166:

Asp Ile Thr Trp Asp Gln Leu Trp Asp Leu Met Lys
1               5                   10

( 2 ) INFORMATION FOR SEQ ID NO:167:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(12)
    ( D ) OTHER INFORMATION: /note= "C-terminal Lys is amidated."

( x i ) SEQUENCE DESCRIPTION: SEQ ID NO:167:

Asp Ile Thr Trp Asp Gln Leu Trp Asp Leu Met Lys
1               5                   10

( 2 ) INFORMATION FOR SEQ ID NO:168:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: one-of(1)
    ( D ) OTHER INFORMATION: /note= "N-terminal Asp is acetylated."

( i x ) FEATURE:
    ( A ) NAME/KEY: Region
    ( B ) LOCATION: one-of(12)
    ( D ) OTHER INFORMATION: /note= "C-terminal Lys is hydroxylated."

(x i) SEQUENCE DESCRIPTION: SEQ ID NO:168:

Asp Ile Thr Trp Asp Gln Leu Trp Lys Leu Met Lys
1               5                   10

(2) INFORMATION FOR SEQ ID NO:169:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Region
    (B) LOCATION: one-of(1)
    (D) OTHER INFORMATION: /note= "N-terminal Asp is modified with benzyloxycarbonyl."

(ix) FEATURE:
    (A) NAME/KEY: Region
    (B) LOCATION: one-of(12)
    (D) OTHER INFORMATION: /note= "C-terminal Lys is amidated."

(x i) SEQUENCE DESCRIPTION: SEQ ID NO:169:

Asp Ile Thr Trp Asp Gln Leu Trp Asp Leu Met Lys
1               5                   10